United States Patent
Evans

(10) Patent No.: US 8,936,471 B2
(45) Date of Patent: Jan. 20, 2015

(54) FLOW RATE MEASURING DEVICE

(71) Applicant: Cheryl L. Evans, Naperville, IL (US)

(72) Inventor: Cheryl L. Evans, Naperville, IL (US)

(\*) Notice: Subject to any disclaimer, the term of this patent is extended or adjusted under 35 U.S.C. 154(b) by 0 days.

(21) Appl. No.: 14/301,294

(22) Filed: Jun. 10, 2014

(65) Prior Publication Data

US 2014/0290380 A1    Oct. 2, 2014

Related U.S. Application Data

(63) Continuation-in-part of application No. 12/705,971, filed on Feb. 15, 2010, now Pat. No. 8,753,124.

(60) Provisional application No. 61/152,726, filed on Feb. 15, 2009.

(51) Int. Cl.
  *G09B 19/00* (2006.01)
  *G01F 1/00* (2006.01)
  *A61B 5/11* (2006.01)
  *A61B 5/00* (2006.01)
  *G01F 1/708* (2006.01)
  *G01F 1/712* (2006.01)

(52) U.S. Cl.
  CPC ... *G01F 1/00* (2013.01); *A61B 5/11* (2013.01); *A61B 5/4205* (2013.01); *G01F 1/708* (2013.01); *G01F 1/7086* (2013.01); *G01F 1/712* (2013.01); *G09B 19/0092* (2013.01)
  USPC ........................................................ 434/127

(58) Field of Classification Search
  USPC ........................................................ 434/127
  See application file for complete search history.

(56) References Cited

U.S. PATENT DOCUMENTS

| | | |
|---|---|---|
| 3,558,898 A | 1/1971 | Block |
| 3,803,903 A | 4/1974 | Lin |
| 3,875,791 A | 4/1975 | Fitzgerald |
| 4,299,119 A | 11/1981 | Fitzgerald |
| 4,484,468 A | 11/1984 | Gau |
| 4,993,365 A | 2/1991 | Weestra |
| 5,503,003 A | 4/1996 | Brookfield |
| 5,932,235 A | 8/1999 | Ninomiya |
| 5,976,084 A * | 11/1999 | Tymchuck .................. 600/300 |
| 6,145,373 A | 11/2000 | Tymchuck |

(Continued)

FOREIGN PATENT DOCUMENTS

WO    WO 2005/117617 A1    12/2005

OTHER PUBLICATIONS

Hembree et al: "Dysphagia evaluation and treatment" Operative Techniques in Otolaryngology-Head and Neck Surgery, W.B. Saunders, vol. 8, No. 4, Dec. 1, 1997.*

(Continued)

*Primary Examiner* — Michael Dennis
*Assistant Examiner* — Dolores Collins
(74) *Attorney, Agent, or Firm* — Chicago IP Law; Steven M. Evans

(57) ABSTRACT

A flow rate measuring device having a housing for enclosing and preventing a removable ramp from being exposed to ambient light. The ramp includes an upper transparent section and a lower transparent section enabling a flowable substance to flow therebetween. A timing circuit connected to a first photo detector and a second photo detector below transparent sections of the ramp determines amount of time for a flowable substance to flow between the first photo detector and the second photo detector. Artificial light sources above the photo detectors are included within the housing.

20 Claims, 24 Drawing Sheets

(56) References Cited

U.S. PATENT DOCUMENTS

| | | | |
|---|---|---|---|
| 6,461,589 B2* | 10/2002 | Robbins | 424/9.41 |
| 6,568,397 B1* | 5/2003 | Addington et al. | 128/897 |
| 6,592,863 B2 | 7/2003 | Fuchs | |
| 6,611,319 B2 | 8/2003 | Wang | |
| 6,683,679 B2 | 1/2004 | Belenkii | |
| 6,887,850 B2 | 5/2005 | Fuchs | |
| 7,238,357 B2* | 7/2007 | Barron | 424/239.1 |
| 7,593,952 B2* | 9/2009 | Soll et al. | 1/1 |
| 7,638,150 B2 | 12/2009 | Holahan | |
| 8,481,000 B2 | 7/2013 | Holahan | |
| 2002/0044957 A1 | 4/2002 | Fuchs | |
| 2003/0044351 A1 | 3/2003 | Robbins | |
| 2004/0197459 A1* | 10/2004 | Gaonkar et al. | 426/601 |
| 2004/0258823 A1 | 12/2004 | Dufresne | |
| 2007/0224126 A1 | 9/2007 | Dufresne | |
| 2009/0162515 A1 | 6/2009 | Dufresne | |
| 2011/0190192 A1* | 8/2011 | Wahren | 514/1.1 |
| 2012/0046641 A1* | 2/2012 | Jedwab et al. | 604/503 |

OTHER PUBLICATIONS

"DDP Guidelines," a dysphagia diet sold by Vocatek, Inc., copyright 1999, 2002, 2006.

Phagia Hand Held Viscometer, sold by Med-Diet Laboratories, 3600 Holly Lane, Suite 80, Plymouth, MN 55447. Publication date of advertisement brochure unknown.

National Dysphagia Diet: Standardization for Optimal Care, American Dietetic Association, 2002.

Development of an objective method for assessing viscosity of formulated foods and beverages for the dysphagic diet, Linda Mann, PDt., and Kwan Wong, PhD, Jounal of the American Dietetic Association, Jun. 1996, pp. 585-588.

Grant by EPSRC, Entitled "A Self-Sensing Instrument for Investigation of Rheology in Dysphagia," Dr. BM Hanson, principal investigator, University College London (Exact publication date unknown).

Balmforth et al., "Viscoplastic dam breaks and the Bostwick consistometer," Journal of Non-Newtonian Fluid Mechanics 142 (2007) 63-78.

Perona, Paolo, "Bostwick Degree and Rheological Properties: An Up-to-Date Viewpoint,"Applied Rheology 15 (2005) 218-229.

Kim, Yoen Kim, thesis as part of requirement for degree of Master of Art, entitled "Inconsistency in the Line Spread Test as an Objective Measurement of Thickened Liquids," Whichita State University, 2007.

Cichero et al., "Which One of These Is Not Like the Others? An Inter-Hospital Study of the Viscosity of Thickened Fluids," Journal of Speech, Language, and Hearing Research, vol. 43, Apr. 2000, pp. 537-547.

Bostwick Consistometer, Arrow Scientific, advertisement on web page http://www.arrowscientific.com.au/bostwick_consistometer.html (original publication date unknown).

Paik NJ et al., Arch Phys Med Rehabil, "Categorization of dysphagia diets with line spread test;" Department of Rehabilitation Medicine, Seoul National University College of Medicine, Seoul, Republic of Korea (May 2004).

Logemann, J.A., "Dysphagia: Evaluation and Treatment", Folia Phoniatrica et Logopaedica, vol. 47, No. 3, 1995.

Hembree et al., "Dysphagia Evaluation and Treatment," Operative Techniques in Otolaryngology-Head and Neck Surgery, W. B. Sanders, vol. 8, No. 4, Dec. 1, 1997.

A. Masters, J.M.Garcia, E.Chambers, "Modified Beverages: Is There Value in the Line Spread Test?"; publication date unknown.

* cited by examiner

FLOW RATE MEASURING DEVICE

CROSS-REFERENCE TO RELATED APPLICATIONS

This patent application is a continuation-in-part (CIP) of application Ser. No. 12/705,971, filed on Feb. 15, 2010, which claims priority and benefit of U.S. provisional patent application having application No. 61/152,726, filed on Feb. 15, 2009, and entitled "Method and Apparatus for Quantifying Dysphagia Foods for Patient Consumption." Both of the patent applications referenced above in this paragraph are hereby incorporated by reference.

FIELD OF THE INVENTION

The present invention relates generally to flow rate measuring devices. More particularly, the present invention relates to a device for measuring the flow rates of flowable foods to facilitate diagnosing and preparing more accurate food diets for dysphagia patients.

BACKGROUND OF THE INVENTION

Dysphagia is a swallowing disorder, wherein a person is unable to swallow or has difficulty swallowing. Dysphagia is known to affect both adults and children, and can be associated with many acquired and neurogenic disorders, such as stroke, Alzheimer's, Cerebral Palsy, Parkinson disease, head and neck cancer, and traumatic brain injury. Left untreated, dysphagia can cause health complications such as aspiration, malnutrition, dehydration, asphyxia, recurrent respiratory infections, and death.

Dysphagia is diagnosed and managed by clinical professionals, typically speech-language pathologists, who are educated in anatomy and physiology of the oral and pharyngeal mechanisms responsible for deglutition. To diagnose and treat dysphagia, patients are often assessed with a comprehensive swallow examination. The examination may include a case history including a patient or family report, an assessment of oral motor, speech and vocal quality, assessment of respiratory function, and an observation of the patient's ability to chew and swallow varying bolus consistencies and sizes. The presence or absence of Dysphagia is often determined through 1) a clinical swallow evaluation or a bedside swallow evaluation and/or 2) a Videofluroscopic Swallow Study (VFSS) or modified barium swallow study (MBS). A bedside swallow evaluation is typically the first step of a comprehensive swallow examination. The patient is evaluated for signs and symptoms of dysphagia such as choking, coughing, gagging, sneezing, drooling, pocketing of food in cheeks, and/or decreased chewing ability. If any sign or symptom of dysphagia is observed, a VFSS may be completed to provide additional information regarding the swallow function.

A VFSS is generally conducted in a radiology suite by a speech-language pathologist in conjunction with a radiologist. The purpose of the VFSS is to confirm there is a dysfunction in the swallowing mechanism, the type of dysfunction (oral, pharyngeal or combination of both), severity of the swallow dysfunction and whether or not aspiration (taking food and liquid into the lungs) is occurring. Once the diagnosis of dysphagia is made and the type and severity are determined, treatment to remediate and/or compensate for the disorder is initiated. Often, dysphagia is diagnosed and treatment initiated based only on the results of a bedside swallow evaluation.

A typical method for therapeutic management of dysphagia is through modifying the consistency of foods and liquids consumed by dysphagia patients. At present date, diet modification is the most commonly used compensatory strategy to manage patients with dysphagia. Foods are routinely altered by adding a commercial thickening agent or thinned by adding water or other thin liquid. Some examples of commercial thickeners include cornstarch and baby cereal.

Currently, foods for dysphagia patients are generally altered to fall within a pre-established category which is named to resemble an approximated consistency, such as honey thickness, nectar thickness and thin liquids. Classification of the liquids and foods for each of the dysphagia diet categories is based on individual, subjective clinical judgment. The conventional method is problematic due to the inherent inconsistencies and ambiguousness of dysphagia diets. A dysphagia diet typically requires all liquids and foods eaten by the patient to be altered in consistency by blending and/or thickening to prevent adverse health consequences. In current practice, there is no set, uniform measurement to determine or replicate the thickness or consistency of the liquids and foods prescribed to a dysphagia patient.

In current practice, to determine the appropriate consistency that a patient can swallow, a therapist pours foods or liquids into a container, adds water or a commercial thickener, and stirs the mixture until the mixture appears to be the proper consistency that the patient can safely swallow without presenting health risks such as aspiration. More water or thickener is added until the therapist visually estimates whether the consistency is appropriate, using his or her best clinical guess. A therapist also may pour the mixture from a spoon to visually estimate the consistency.

The mixture is then classified into one of predetermined groups, such as (1) "honey" thickness, (2) "nectar" thickness or (3) "thin," depending on what the mixture consistency most resembles. If a dysphagia diet is prescribed and a liquid consistency is deemed appropriate for the patient, the patient is instructed to drink only one of the predetermined classifications of consistency prescribed, and no other consistency, because other consistencies could be aspirated.

Aspiration can have serious and deadly consequences to a patient's health, such as causing pneumonia, weight loss, fevers, recurrent respiratory illness, or even death. Unfortunately, without a consistent, quantifiable measurement system, the perception of "honey," "nectar" and "thin" liquids is so variable between people that they are rarely the same. Even the same therapist can mix two separate batches of liquids and foods and have resulting variations in the consistency. For a patient, such variations can be deadly.

Further adding to the problem, dysphagia patients are routinely transferred between medical facilities in clinical care, each with their own guidelines of what constitutes a particular consistency. Routinely, as dysphagia patient's conditions improve, they are transferred to different departments or facilities such as acute care, sub-acute care, rehabilitation facility, long-term (nursing home) care facility or to their home. The potential for problems, in terms of continua of care, increases with each transfer between treatment locations because of variability between caregivers in their perception of food consistencies. A specific technical problem is the inability for a patient or their caregiver to quantifiably replicate the appropriate food consistency prescribed to the patient that would reduce adverse health risks due to their swallow dysfunction.

Current and common methods of treatment include: 1) providing patients with written descriptive diet plans containing examples of recommended foods and liquids, or 2) recommending purchase of a particular commercially prepared product based on its viscosity. Neither of these current treatment methods is optimal. In written descriptive diets, the preparer of the dysphagia diet food and/or liquids are required to estimate the appropriate consistency or viscosity by visually comparing it to another similar food item. In commercially prepared products, manufacturers use different techniques and machinery which are not consistent between manufactures. Consequently, manufacturers of dysphagia food products have different standards of consistency and viscosity, and furthermore, often use the same nomenclature for the categories, such as honey thick, nectar thick or thin liquids. Because of these inconsistencies, the patients may inadvertently consume an inappropriate consistency if they use products from different manufacturers, placing themselves at risk for aspiration or other health consequences.

Presently, there is no technique, procedure or method for clinical professionals, caregivers or patients to independently determine acceptable prescribed foods and liquids based on objective measures.

While the exact number of people suffering from dysphagia is unknown, a sampling survey conducted by the National Center for Health Statistics reported out of 77 million hospitalizations from 2004-2005, 35% were associated with dysphagia.

Accordingly, there is a strong need for a quantitative measurement system that can easily measure food characteristics for dysphagia patients, enabling foods to be reproduced having consistent properties, regardless of the manufacturer, therapist, caregiver or patient preparing the food. There also is a need for dysphagia diets that more precisely meet the specific needs of each dysphagia patient.

Aspects and Summary of the Invention

In view of the forgoing, an aspect of the present invention is to provide a method for quantifying a customized dysphagia food diet for a patient, instead of forcing the patient into one of a group of predetermined dysphagia diets that may not be suitable for the specific needs of that dysphagia patient.

Another aspect of the present invention is to provide a method for more accurately defining the type and severity of a patient's particular dysphagia.

A further aspect of the present invention is to provide a method for prescribing a customized dysphagia diet that fits the specific needs of a dysphagia patient, instead of placing the patient into one of a group of "one-size-fits-all" predetermined dysphagia diets.

An additional aspect of the present invention is to provide an apparatus enabling a medical professional to more accurately define the type and severity of a patent's dysphagia.

In that regard, a further aspect of the present invention is to provide an apparatus to enable a medical professional to prescribe a dysphagia diet that is customized to more accurately address the specific type and severity of a patient's dysphagia.

Another aspect of the present invention is to provide an apparatus that enables a treating speech therapist, caregiver, or patient to prepare or reproduce foods that are more accurately consistent with the prescribed dysphagia diet for a particular patient.

Furthermore, an aspect of the present invention is to provide an inexpensive and durable apparatus that accurately measures a quantifiable characteristic of liquid foods that enables the diagnosing professional to prescribe a customized dysphagia diet that addresses the needs for the specific type and severity of a patient's dysphagia, and then even further, enables a treating professional, caregiver, or the patient to accurately reproduce foods consistent with the parameters of the prescribed customized dysphagia diet for that particular patient.

Additional aspects of the present invention include (1) enabling patients to eliminate the cost of expensive prepackaged, commercially prepared food and liquid products, (2) enabling patients to make safe food and liquid choices, (3) enabling patients to stay within the confines of a prescribed quantified food characteristic range, (4) allowing patients to prepare foods and drinks at home that are more preferable to their specific taste and/or ethnic background than commercially prepared foods, and (5) eliminating health risks associated with consumption of inappropriate consistencies caused by using products from different manufacturers. It should be noted that the word "food" in this application refers to solid foods and liquid foods.

In order to achieve the aspects set forth above, the present invention provides an apparatus having a housing for enclosing and preventing a ramp from being exposed to ambient light. The ramp is removable from the housing and has transparent portions over first and second photo detectors. The first photo detector detects flowable substances passing over the first photo detector, and the second photo detector detects flowable substances passing over the second photo detector. A timing circuit is connected to the first photo detector and the second photo detector, wherein the timing circuit determines amount of time for a flowable substance to flow between the first photo detector and the second photo detector. A first light source is located over the first photo detector, and a second light source is located over the second photo detector. A display is located on the housing for displaying elapsed time for a flowable substance to flow between the first photo detector and the second photo detector as determined by the timing circuit. The angle of the ramp can vary, but the inventor has found an angle of about 35 degrees to work well. Additionally, the present invention can be used to time moving objects traveling down a ramp, such as rolling balls.

Other features and advantages of the present invention will become apparent to those skilled in the art from the following detailed description. It should be understood that the detailed description and specific examples, while indicating the preferred embodiment of the present invention, are given by way of illustration and not limitation. Many changes and modifications within the scope of the present invention may be made without departing from the spirit of the invention, and the invention includes all such modifications.

DETAILED DESCRIPTION OF THE PREFERRED EMBODIMENTS

Figure 1:
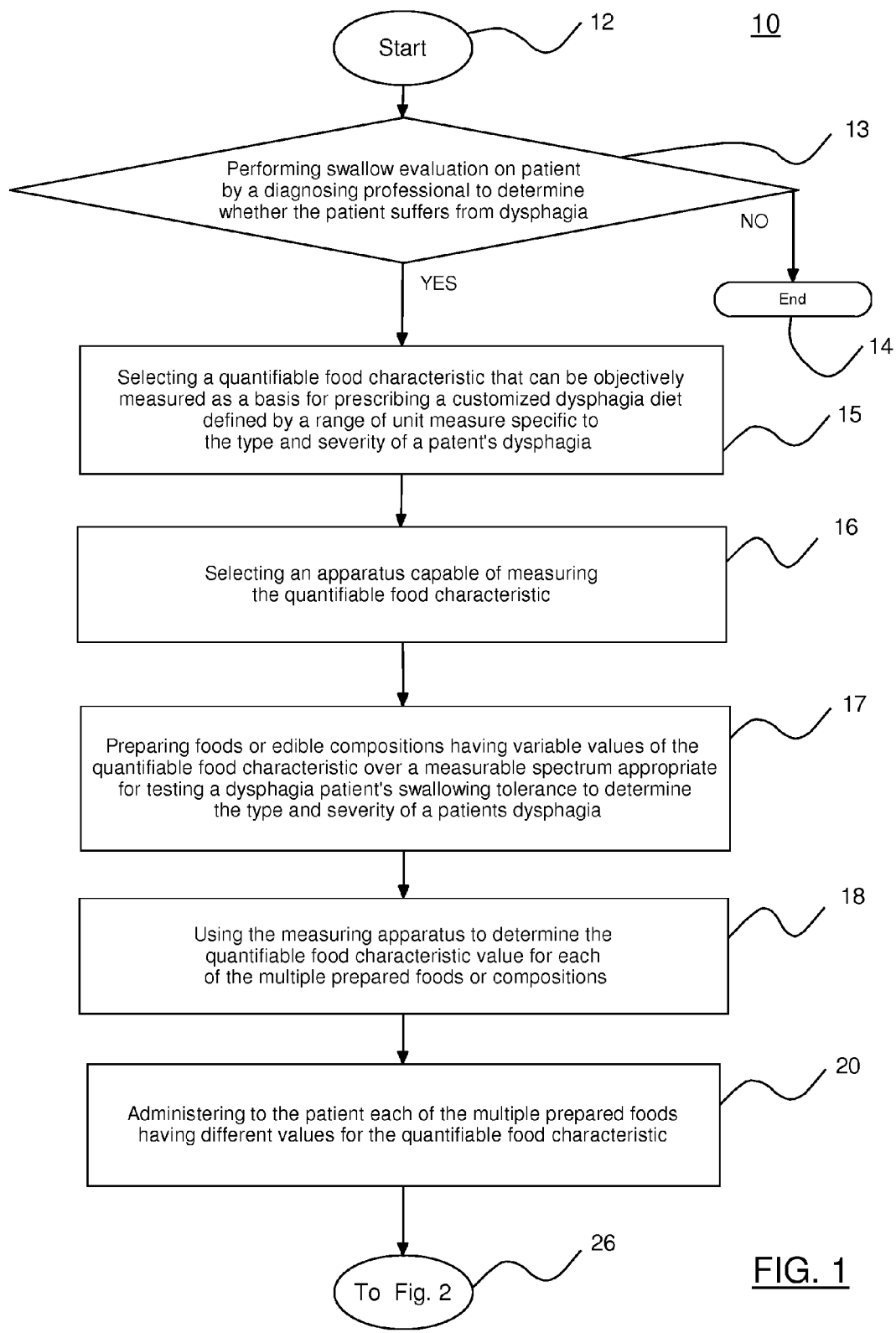
FIG. 1 is a flowchart of a preferred method of the present invention.
Figure 2:
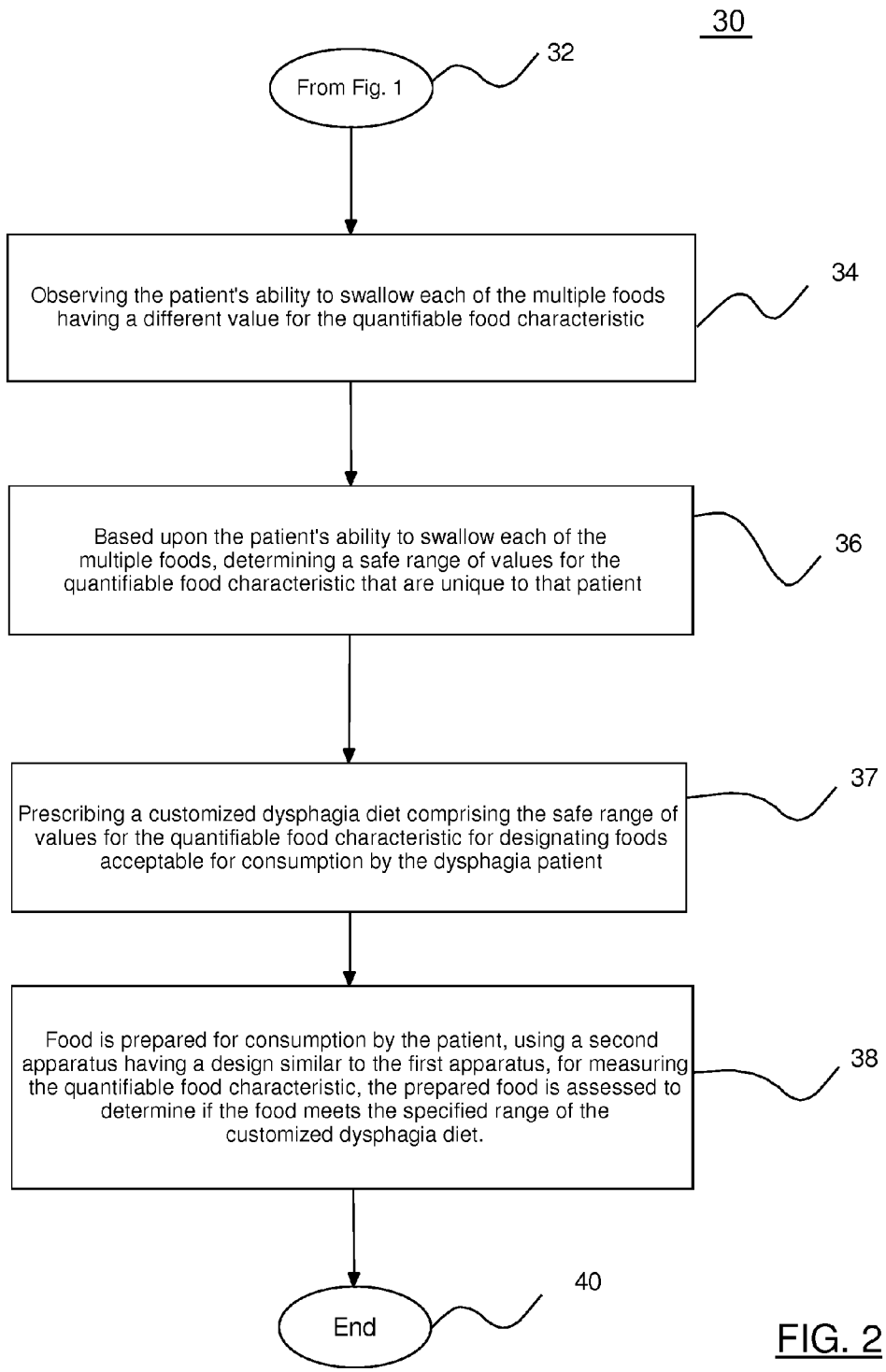
FIG. 2 is a continuation of the flowchart shown in FIG. 1.

Referring now to the drawings, FIGS. 1 and 2 are a flowchart of the preferred method of the present invention. The flowcharts 10 and 30 illustrate the steps for evaluating and diagnosing the type and severity of a patient suffering from dysphagia. The flowcharts 10 and 30 further illustrate a process for prescribing a customized dysphagia diet for a patient and a process for reproducing foods consistent with the customized dysphagia diet.

Beginning at the start 12, a patient is first evaluated at step 13 to determine if the patient is suffering from dysphagia. If the test is negative, the process terminates at step 14. If the swallowing evaluation at step 13 indicates the patient is suffering from dysphagia, the process moves to step 15.

In accordance with the present invention at step 15, a quantifiable food characteristic is selected that can be objectively measured as a basis for prescribing a customized dysphagia diet defined by a range of unit measure specific to the type and severity of a patient's dysphagia. For example, a quantifiable food characteristic could be flow rate or viscosity at room temperature.

Next at step 16 an apparatus is selected for measuring the selected quantifiable food characteristic. For example, a Bostwick consistometer can be used to measure quantifiable food characteristics such as consistency, viscosity, and/or flow rate. A viscometer can be used to measure the quantifiable food characteristic of viscosity. The line spread test can be used to measure flow rate on a flat surface. Preferably, the quantifiable food characteristic, such as flow rate, could be measured using one of the novel measuring apparatuses described in this application.

Next at step 17 foods or edible compositions (such as a barium mixture used in a VFSS) are prepared having variable values of the quantifiable food characteristic over a measurable spectrum appropriate for testing a dysphagia patient's swallowing tolerance to determine the type and severity of a patient's dysphagia.

At step 18 the selected apparatus is used to determine the quantifiable food characteristic value for each of the multiple prepared foods or compositions. Next at step 20, the diagnosing professional administers to the patient each of the multiple prepared foods having different values for the quantifiable food characteristic.

FIG. 2 illustrates the next step 34, wherein the diagnosing professional or speech pathologist observes the patient's ability to swallow each of the multiple foods having a different value for the quantifiable food characteristic, such as flow rate.

Based upon the patient's ability to swallow each of the multiple foods, at step 36 the diagnosing professional determines a safe range of values for the quantifiable food characteristic that are unique or customized for the patient to more accurately and precisely define foods acceptable for consumption by the patient.

At step 37 the diagnosing professional prescribes a customized dysphagia diet comprising the safe range of values for the quantifiable food characteristic for designating foods acceptable for consumption of the dysphagia patient. For example, a customized diet of foods having flow rates within a quantifiable range of flow rates.

At step 38 foods are prepared for consumption by the patient, using a second apparatus having a similar design to the first apparatus that measures the quantifiable food characteristic that enabled the diagnosing professional to prescribe a customized diet for the patient. By using an apparatus similar to the apparatus used in measuring the quantifiable foods for diagnosing the patient, the patient can easily and accurately reproduce foods that are consistent with the patient's prescribed dysphagia diet.

Figure 3:
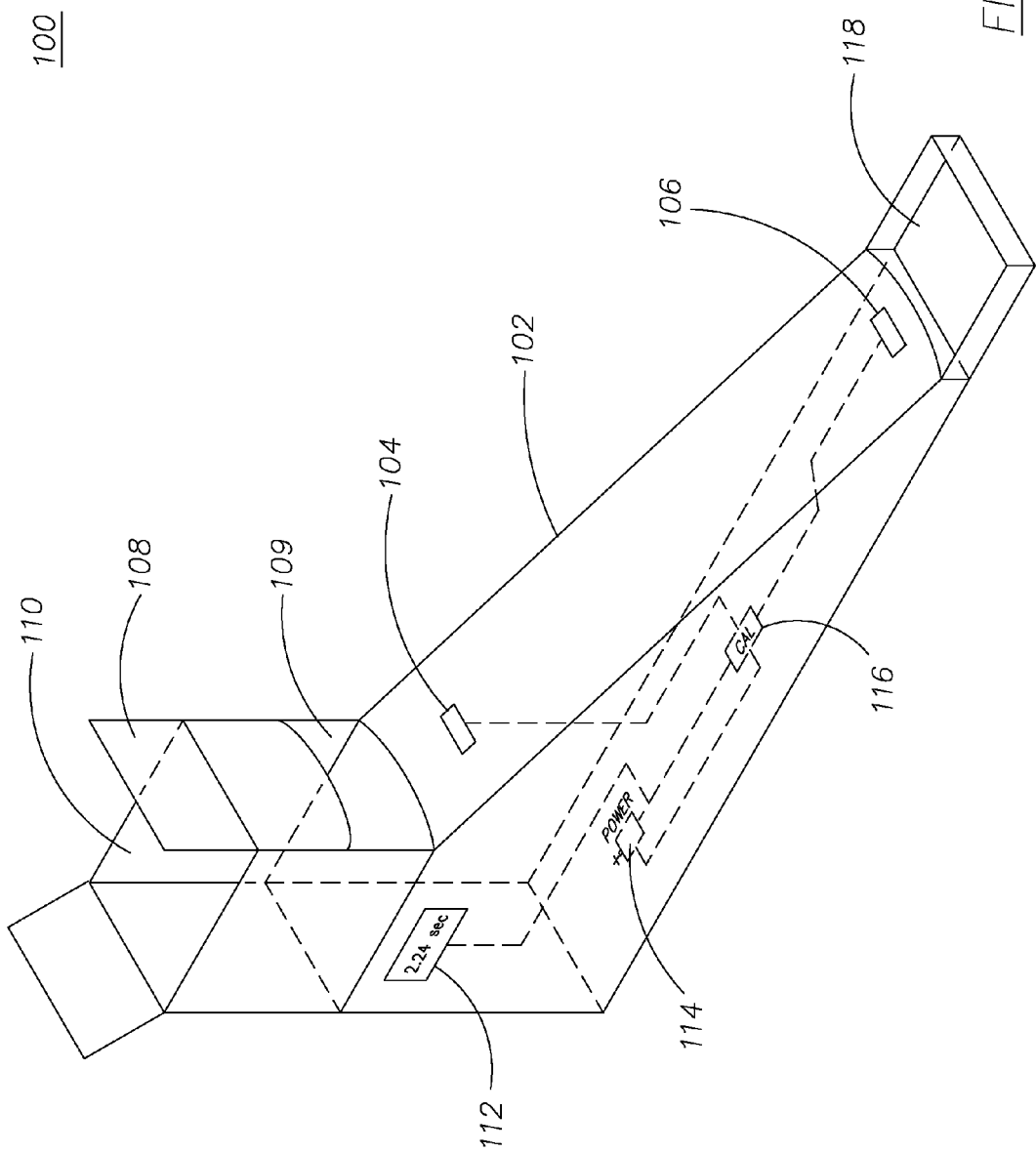
FIG. 3 is a perspective view of a flow rate measuring device constructed in accordance with a first embodiment of the present invention.

FIG. 3 illustrates a perspective view of a flow rate measuring device 100 configured in accordance with a first embodiment of the present invention. The flow rate measuring device 100 has a ramp or chute 102 that includes a first liquid sensor 104 and a second liquid sensor 106. The liquid sensors 104, 106 are located in the lower floor or curved section of the chute 102. Preferably, the liquid sensors 104, 106 are covered with glass plates located within apertures in the chute 102, enabling the liquid sensors 104, 106 to optically detect liquid as it flows over the liquid sensor 104 and then the liquid sensor 106. The liquid sensors 104, 106 can be of a type disclosed in U.S. Pat. Nos. 3,558,898; 6,683,679; or 6,611,319, all of which are hereby incorporated by reference.

The upper portion of the chute 102 is connected to a reservoir or retention area 110. A vertical sliding gate 108 is formed into a wall of the retention area 110. The gate 108 can be slid up to create an opening 109 which allows liquid contained within the retention area 110 to flow down the chute 102. When the gate 108 is opened, liquid in the retention area 110 is released and flows down the chute 102 into a receiving receptacle 118. When the gate 108 is opened, liquid from the retention area 110 will first pass over the first liquid sensor 104 and then over the second liquid sensor 106. An electronic timer/calculator 116 electrically connected to the liquid sensors 104 and 106 determines the elapsed time for the liquid to flow between liquid sensors 104 and 106. The time is displayed upon a display 112. The calculator 116 can be similar to the design disclosed in the electronic time-correlating system of U.S. Pat. Nos. 3,558,898; 6,683,679; or 6,611,319, all of which are hereby incorporated by reference. A battery 114 can be used to provide power to the timer 116 and sensors 104,106.

Figure 4:
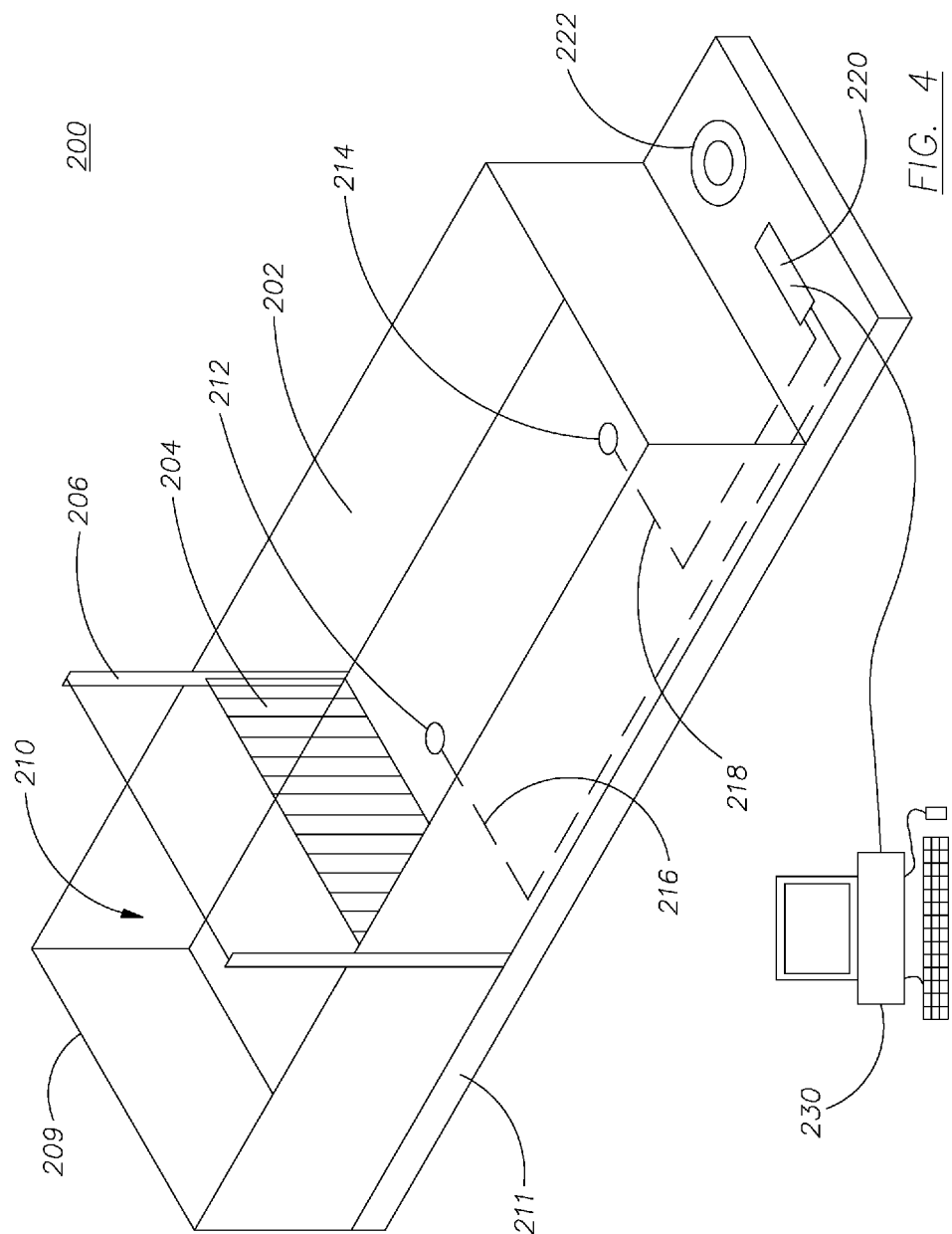
FIG. 4 is a perspective view of a flow rate measuring device configured in accordance with a second embodiment of the present invention.

FIG. 4 illustrated another flow rate measuring device 200 configured in accordance with a second embodiment of the present invention. The flow rate measuring device 200 is similar to a Bostwick consistometer with some additional improvements. A chute 202 is provided that can be constructed out of plastic or metal. The chute 202 includes a first liquid sensor 212 and a second liquid sensor 214, which may be similar to the liquid sensors 104,106 discussed above. The first and second liquid sensors 212,214 are preferably photo detectors, photo sensors, optical detectors, optical sensors, or any type of sensor capable of detecting presence or absence/decrease of light. Additionally, if the first and second liquid sensors are a type of light sensor, the detected light can be from, and is not limited to, any particular spectrum of light. For example, the sensors 212,214 could detect visible light, or ultraviolet light, or both. The liquid sensors 212, 214 are preferably flush with the surface of the chute 202, or covered by a transparent plate that protects the liquid sensors 212,214 and is flush with the surface of the chute 202 to avoid interfering with the flow of a liquid in the chute 202.

A bubble level 222 is included for leveling a base 211 of the chute 202. Electrical connections 216 and 218 from the liquid sensors 212 and 214, respectively, electrically connect the liquid sensors 212 and 214 to a connector 220. The connector 220 can be a USB socket or similar computer connector.

A vertical sliding gate 204 is located in the chute 202 near a first end wall 209 of the chute 202. A retention area or reservoir 210 is formed by the gate 204 and the end wall 209 of the chute 202. The gate 204 is opened by sliding up along a runner 206. When the gate 204 is opened, liquid contained within the retention area 210 flows out along the chute 202, first over liquid sensor 212 and then over liquid sensor 214, wherein each liquid second 212,214 sends a liquid detection signal to a personal computer 230 that is electrically connected to the sensors 212,214 via the connector 220. The personal computer 230 provides power to the liquid sensors 212,214 and also performs the timing calculations to determine the time it takes for liquid to flow between liquid sensor 212 and liquid sensor 214. The computer 230 also functions as a display for indicating the time interval for the liquid to flow between liquid sensors 212 and 214. The computer 230 can be programmed to perform far more complicated tasks, such as managing multiple test trials, multiple patient data, and correlating flow data with different food types. An advantage of the flow rate measuring device 200 is the reduced cost to a consumer, be it a patient or speech pathologist, of the flow rate measuring device 200 because most of the electronics are located in the personal computer 230, which would typically already be owned by the consumer, and thus would not need to be included within the chute 202 component of the flow rate measuring device 200.

Figure 5:
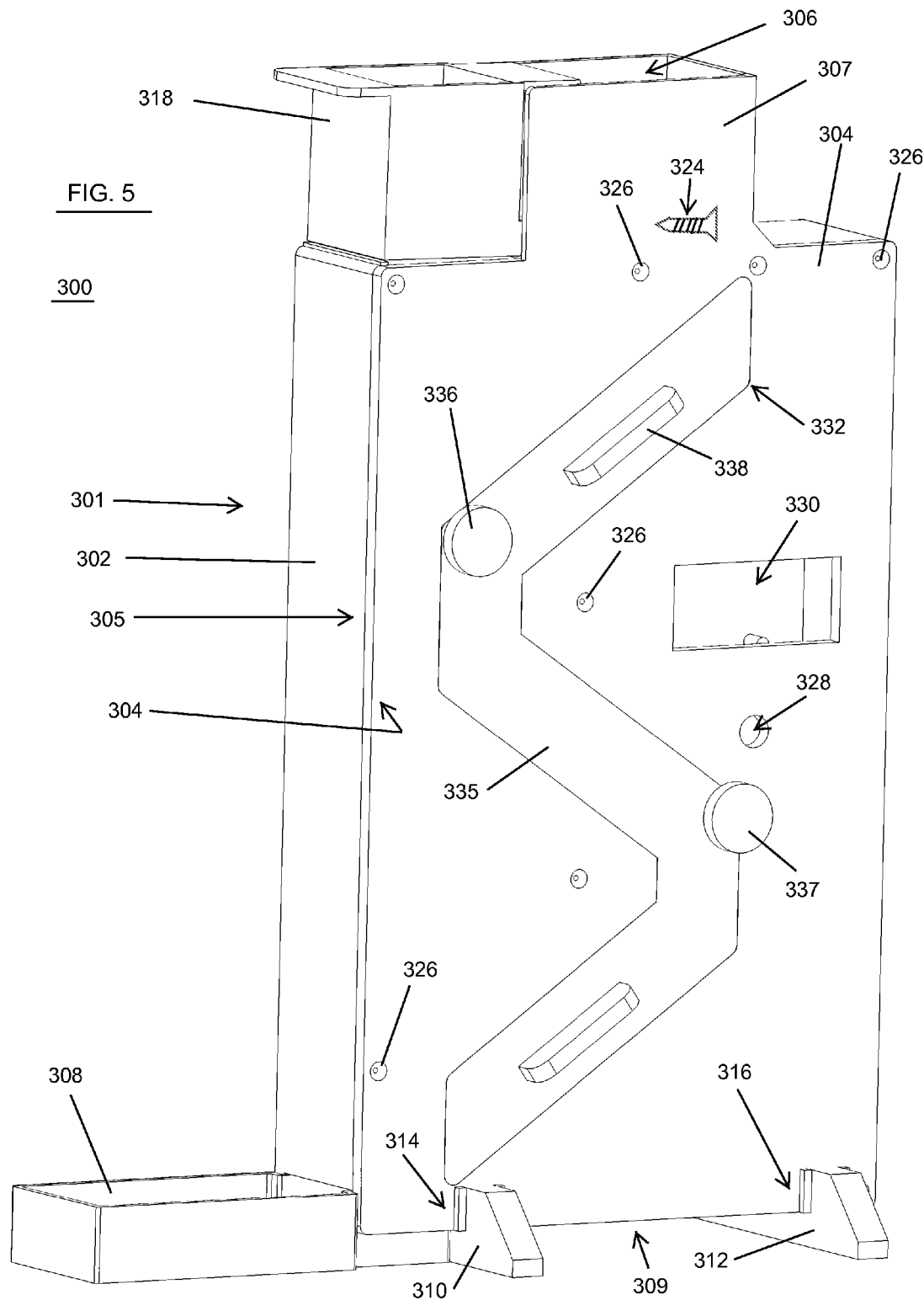
FIG. 5 is a perspective view of a flow rate measuring device configured in accordance with a third and preferred embodiment of the present invention.
Figure 6:
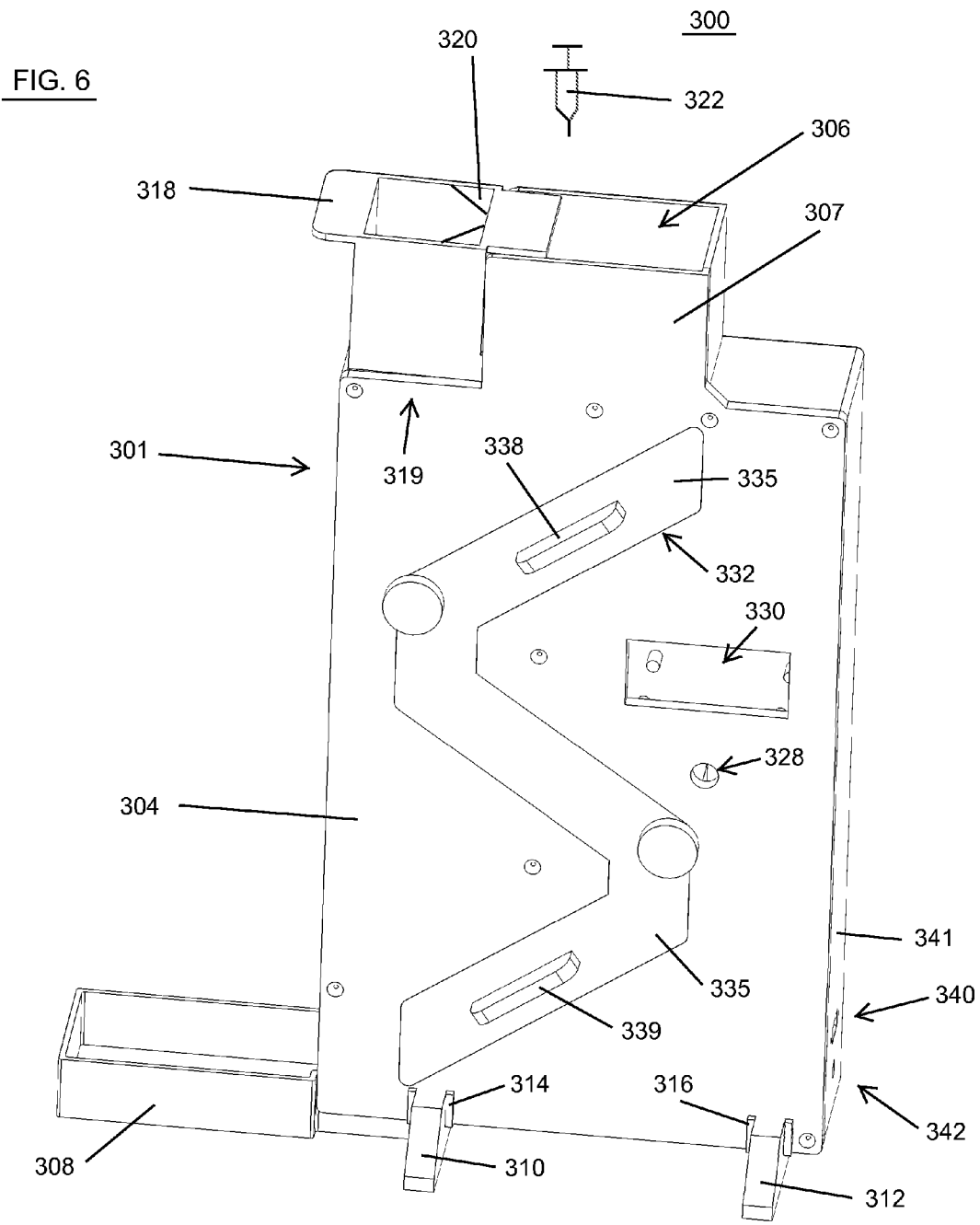
FIG. 6 is a perspective view of the flow rate measuring device shown in FIG. 5 from a higher elevation.

Turning now to a third embodiment of the present invention, FIGS. 5 and 6 illustrate a flow rate measuring device 300 configured in accordance with the present invention. FIG. 5 is a perspective view of the measuring device 300 from the same elevation, and FIG. 6 is a perspective view of the measuring device 300 looking down from a higher elevation. The flow rate measuring device 300 includes a housing 301 having a body 302 and a cover plate 304 on a front 305 of the body 302. An input port 306 for inputting and testing flowable food is located at a top 307 of the device 300, and a catch tray 308 is located at a bottom 309 of the device 300. Legs 310 and 312 are attached to the bottom 309 of the device 300 in order to stabilize the device 300. The legs 310 and 312 fit into slots 314 and 316 on the bottom 309 of the device 300.

A tip cup 318 is pivotally mounted to the upper portion 319 of the device 300. Flowable food to be tested by the device 300 initially can be placed within the tip cup 318, which is then rotated to pour the flowable food into the input port 306. A curved or circular insert 320 preferably is located within the tip cup 318 to direct poured flowable food into the center of the input port 306.

A syringe 322 also can be used to directly inject flowable food into the input port 306. The syringe 322 can dispense precise quantities of flowable food or other liquid into the input port 306 of the measuring device 300. Furthermore, the syringe 322 reduces the risk of spillage of liquid or flowable food being inputted into the input port 306.

The cover plate 304 preferably is secured to the front 305 of the body 302 of the flow rate measuring device 300 by screws 324 being inserted into screw holes 326 in the cover plate 304. The screws 324 are screwed into brackets, posts, and the perimeter of the body 302 of the measuring device 300. The cover plate 304 includes an aperture 328 for a reset button and a cutout 330 for a display panel, which are part of the electronic circuitry to be included within the measuring device 300. A diagonal cutout 332 also is located within the cover plate 304 for receiving a ramp 335. The ramp 335 carries the flowable food during testing. The ramp 335 is designed to be removable from the housing 301 of the measuring device 300 for cleaning. The ramp 335 includes first and second securing knobs or bolts 336,337 for securing the ramp 335 within the housing 301, and first and second handles 338,339 for removing the ramp 335 from the housing 301. A cutout 340 is included on the side 341 of the body 302 of the measuring device 300 for a data communication port, such as a USB port. Another cutout 342 is included on the side 341 for an on/off switch for activating internal electrical components, such as internal lighting of the ramp 335 and timing circuitry, which will be discussed below.

Figure 7:
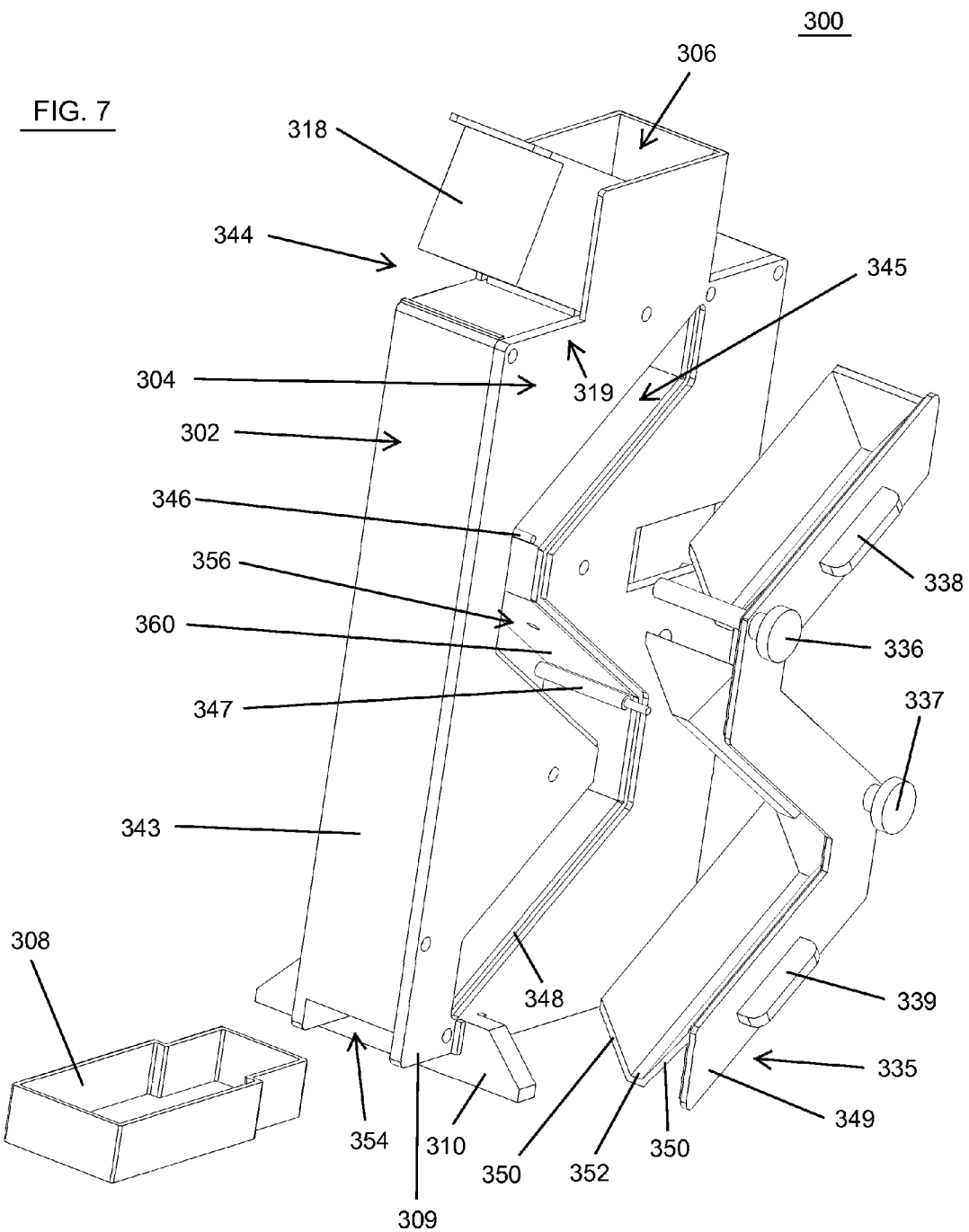
FIG. 7 is an exploded view of the flow rate measuring device shown in FIGS. 5 and 6.
Figure 8:
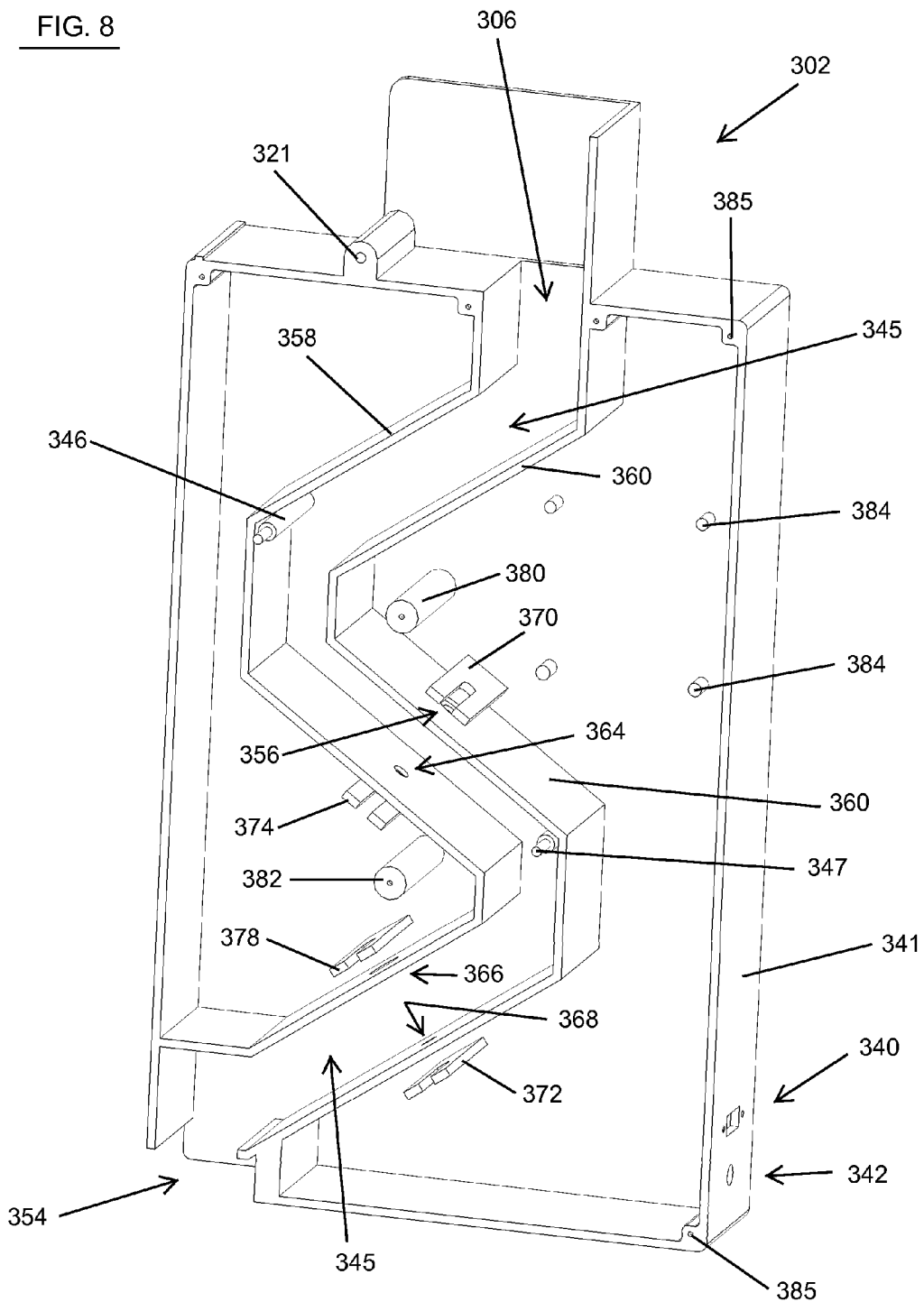
FIG. 8 is a perspective view of the flow rate measuring device shown in FIGS. 5-7 without the front cover plate, ramp, tip cup, and catch tray.

FIG. 7 is an exploded view of the flow rate measuring device 300 shown in FIGS. 5 and 6. The tip cup 318 is shown being rotatably or pivotally mounted 344 to the top or upper portion 319 and adjacent to the input port 306 for pouring in a predetermined amount of flowable food or liquid to be tested by the measuring device 300. The ramp 335 is configured to be inserted into a zigzag receptacle 345 in the housing 301, and to be removable using the handles 338,339. The ramp 335 is secured within the receptacle 345 using screw knobs 336,337. The screw knobs 336,337 connect to mounting posts 346,347, respectively, to secure the ramp 335 within the receptacle 345, and also allow removal of the ramp 335 for cleaning.

The receptacle 345 is configured to keep the ramp 335 within the housing 301 and prevent the ramp 335 from being exposed to ambient light. A ridge 348 is formed in the edges of the receptacle 345 to mate with the cover plate 349 of the ramp 335 and form a seal preventing ambient light from entering the receptacle 345 and falling onto the inside of the ramp 335.

The ramp 335 includes inclined sides 350 and a flat floor 352 at the bottom of the inclined sides 350. An opening 354 is included in the bottom 309 of the measuring device 300 from which flowable food flowing down the ramp 335 exits the ramp 335 and is collected by the catch tray 308. The catch tray 308 also is removable for cleaning. An aperture 356 is located in a second wall 360 of the receptacle 345 enabling artificial light from an internal light source to shine on the floor 352 of the ramp 335 when the ramp 335 is located within the receptacle 345.

FIGS. 8-11 are perspective views of the inside of the body 302 of the flow rate measuring device 300. The inside of the body 302 is exposed as the cover plate 304 shown in FIGS. 5-7 is removed. The catch tray 308, tip cup 318, ramp 335, stabilizer legs 310,312, and cover plate 304 are not shown in FIGS. 8-11 in order to better illustrate the inside of the housing 301. The pivot or rotatable mount 321 for the tip cup 318 also is clearly illustrated.

In accordance with the present invention, a receptacle 345 is provided within a housing 301 for shielding the inside of a ramp 335 from ambient light. Artificial light sources inside the housing 301 and above the ramp 335 shine down on photo detectors below the ramp 335 to detect when a flowable food or liquid passes over each photo detector. If necessary, a substance is added to the flowable food or liquid in order to darken or opaque the flowable food or liquid to better enable the photo detectors to detect passing flowable food or liquid if the flowable food or liquid is originally clear or transparent. By using an artificial light source inside a controlled lighting environment, such as the housing 301, the accuracy of the flow rate measuring device 300 can be improved.

FIGS. 8-11 illustrate the zigzag configuration of the receptacle 345, which follows the configuration of the ramp 335. The zigzag configuration of the ramp 335 increases the length of the ramp 335 available inside the housing 301. Additionally, the zigzag design of the ramp 335 functions to control the flow rate of liquids being tested. While preferred, the zigzag design of the ramp 335 is not required, and the ramp 335 could be a linear, circular, or even a corkscrew configuration.

The receptacle 345 includes a first wall 358 and a second wall 360, which zigzags back and forth to follow the path of the ramp 335, which is to be secured inside the receptacle 345. The first wall 358 includes apertures 364 and 366. Aperture 364 is for a photo detector, and aperture 366 is for an artificial light source, such as an LED. Similarly, the second wall 360 includes an aperture 356 for an artificial light source and an aperture 368 for a photo detector. Bracket 370 is for mounting a light source above aperture 356, and bracket 372 is for mounting a photo detector below aperture 368. Bracket 374 is for mounting a photo detector below aperture 364, and bracket 378 is for mounting an artificial light source above aperture 366.

Posts 380 and 382 are for securing the cover plate 304 to the front 305 of the body 302 using screws. Four posts 384 are for mounting a printed circuit board (PCB) inside the housing 301. The PCB 400 (FIG. 13) includes a display 402 which is viewed through the cutout 330 (FIG. 5). Screw holes 385 are included in the body 302 for securing the cover plate 304 to the body 302.

Figure 9:
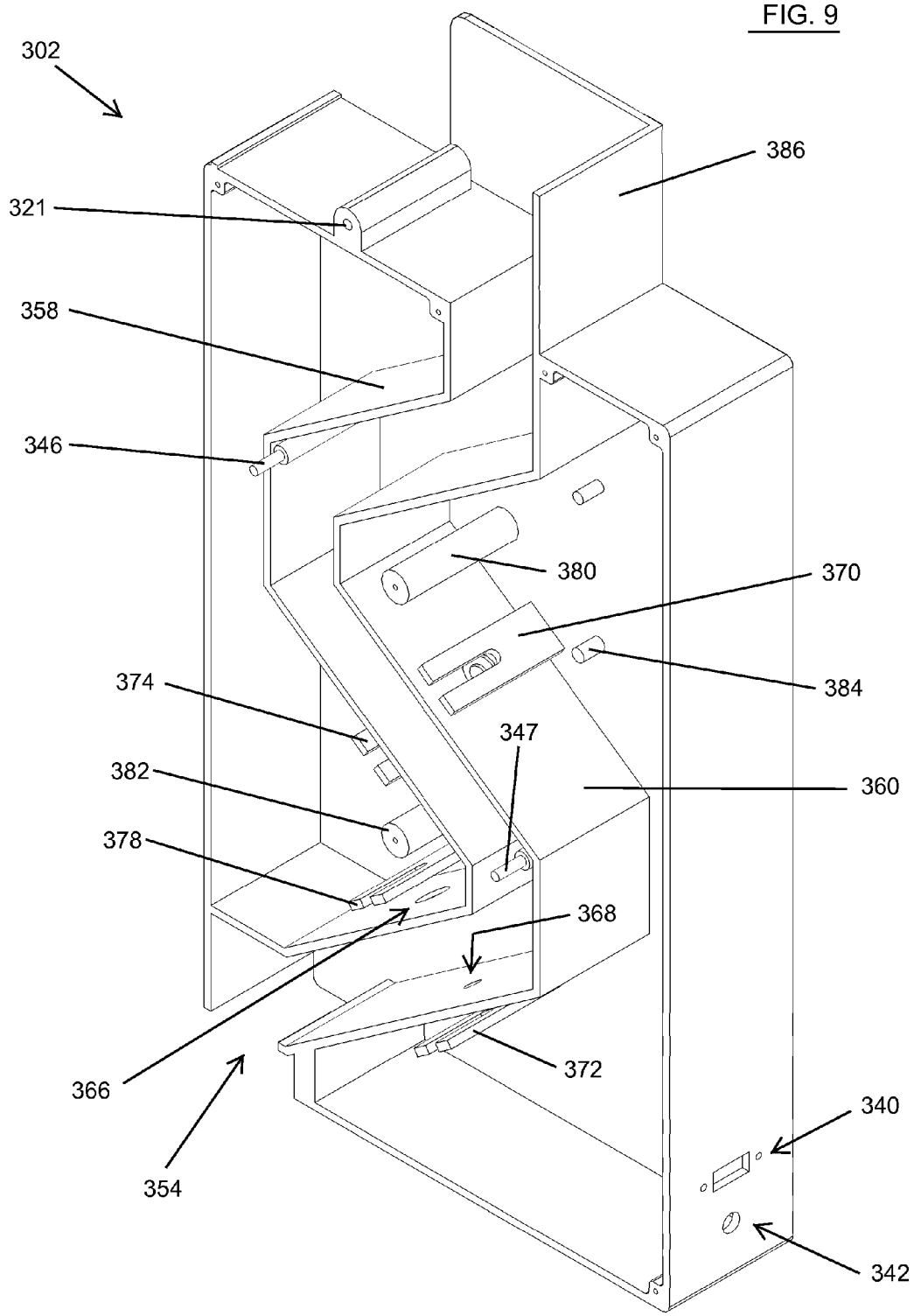
FIG. 9 is a perspective view of the flow rate measuring device shown in FIG. 8 from a different angle.
Figure 10:
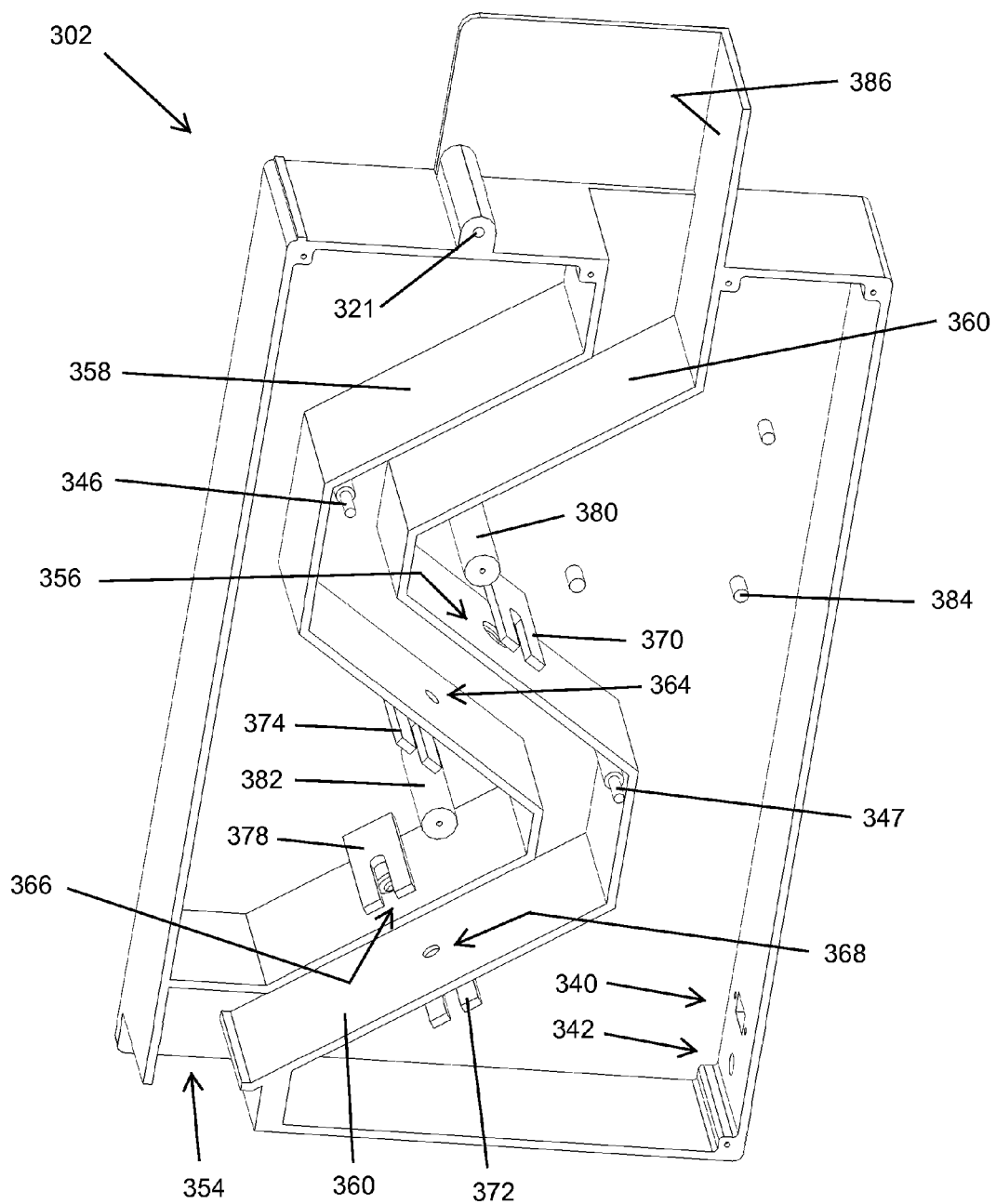
FIG. 10 is a perspective view of the flow rate measuring device shown in FIGS. 8 and 9 from a different angle.
Figure 11:
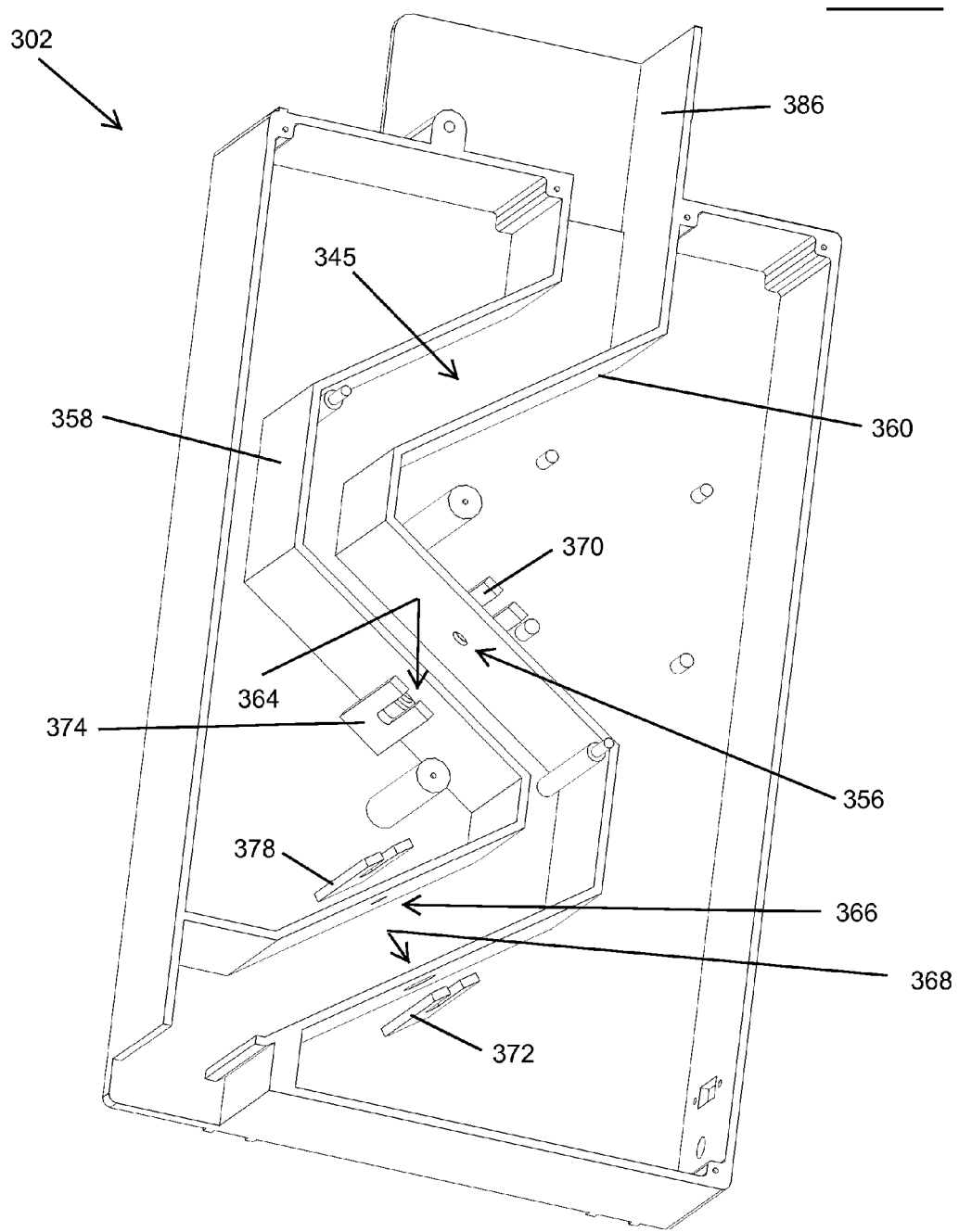
FIG. 11 is a perspective view of the flow rate measuring device shown in FIGS. 8-10 from a different angle.

A splash guard 386 and pivot mount 321 are better illustrated in FIG. 9. The pivot mount 321 is for the tip cup 318. The splash guard 386 functions to prevent liquids from missing the input port 306 when the tip cup 318 is tilted up and over. Aperture 340 for a data port and aperture 342 for a power switch are shown on side 341 of the body 302.

Figure 12:
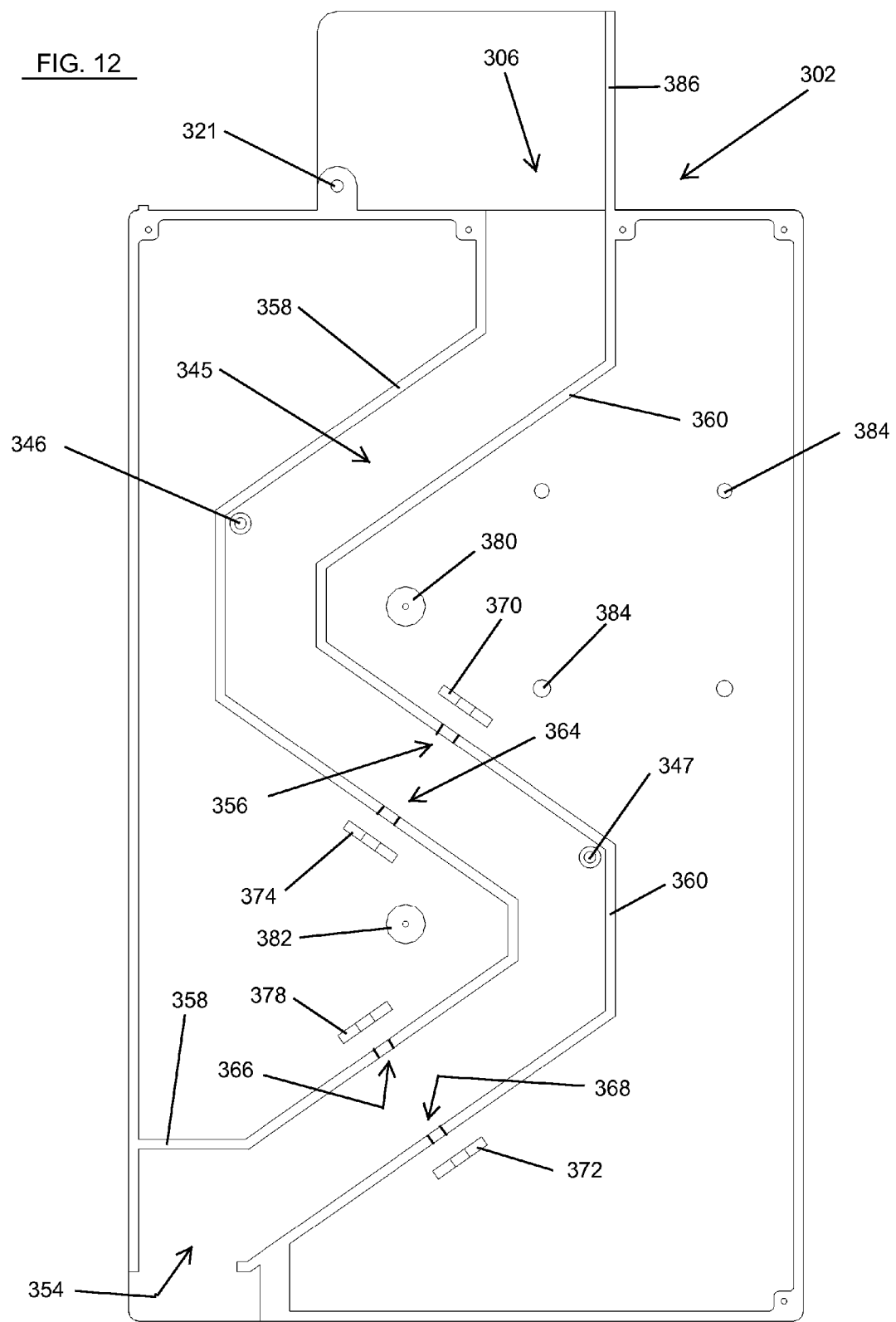
FIG. 12 is a front view of the flow rate measuring device shown in FIGS. 8-11.

FIG. 12 is a front view of the body 302 shown in FIGS. 8-11. FIG. 12 provides a front view of the receptacle 345 and the first wall 358 and the second wall 360. The apertures 364, 368 and mounting brackets 374, 372, respectively, for the photo detectors are illustrated. The apertures 356, 366 and mounting brackets 370, 378, respectively, for the artificial lights sources also are illustrated.

Figure 13:
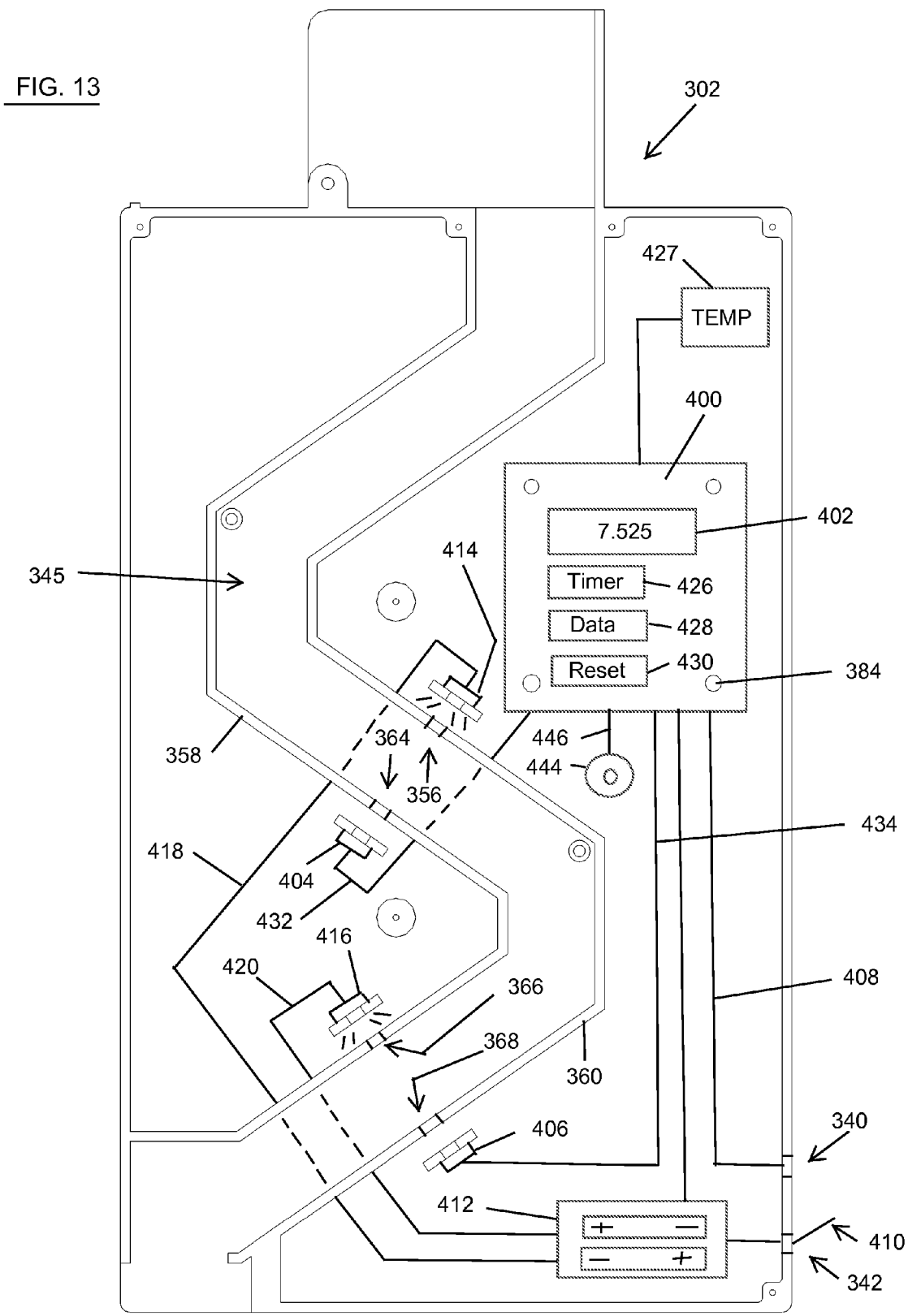
FIG. 13 is a front view of the flow rate measuring device shown in FIG. 12, wherein electronic components have been included.

FIG. 13 is a front view of the body 302 of the flow rate measuring device 300 shown in FIG. 12, except electrical components for the timing mechanism have been added to FIG. 12. A printed circuit board 400 having a display 402 is shown mounted to the posts 384 inside the body 302 of the flow rate measuring device 300. The display 402 is sized to fit and show through the cutout 330 of the cover plate 304. The display 402 displays the calculated time for a liquid or flowable food to pass between apertures 364 and 368 along the ramp 335 to be located within the receptacle 345, as detected by photo detectors 404 and 406, respectively.

The first and second liquid sensors 404 and 406, respectively, are preferably photo detectors, optical detectors, or optical sensors, or any type of sensor capable of detecting presence or absence/decrease of light. Additionally, light detected by the photo detectors 404 and 406 can be from and is not limited to any particular spectrum of light. For example, the photo detectors 404 and 406 can detect visible light, or ultraviolet light, or both.

Data port 340 is electrically connected to the PCB 400 via a data wire 408. A power switch 410, such as a toggle switch, is located in the aperture 342 to enable electrical current to flow from an internal power source 412, such as a couple of 1.5 volt batteries, to light sources 414 and 416, which are preferably light emitting diodes (LEDs). The light sources 414 and 416 are powered via wires 418 and 420, respectively.

In accordance with a preferred embodiment of the present invention, the ramp 335 is placed and secured within the receptacle 345, and ambient light is prevented from reaching the ramp 335 within the receptacle 345. The ramp 335 includes apertures 422 and 424 (FIG. 22) filled with transparent windows, and the apertures 422 and 424 are to be located directly over the apertures 364 and 368 when the ramp 335 is placed within the receptacle 345. LEDs 414 and 416 shine light through apertures 356 and 366 onto photo detectors 404 and 406, respectively, through apertures 364 and 368. The amount of light shown onto the ramp 345 by the LEDs 414 and 416 is precisely controlled via size of apertures 356 and 366 and type and location of LEDs 414 and 416.

When a flowable liquid passes over the first photo detector 404, a timer circuit 426 located on the PCB 400 begins running and displays elapsing time on display 402. When the liquid passes over the second photo detector 406, the timer circuit 426 stops running and displays the elapsed time on the display 402. Light received by the first photo detector 404 only needs to be briefly interrupted or decreased to start the timer 426 and running time on the display 402; light can be received by the first photo detector 404 after starting the timer 426, but the timer 426 and display 402 do not stop running until the second photo detector 406 detects an interruption or decrease in received light due to liquid passing over aperture 368.

The timer 426 and display 402 preferably can clock time intervals in thousandths of seconds and up to at least several minute internals. Furthermore, the PCB 400 includes include an electronic thermometer 427, and the display 402 indicates the current ambient temperature, thereby enabling an operator of the flow rate measuring device 300 to obtain consistent results, such as testing flow rates at a predetermined room temperature. If the flowable food to be tested is not at ambient temperature, the user can manually measure the food to be tested using an external thermometer to confirm it is at a desired temperature before being tested.

The photo detectors 404 and 406 detect a reduction or loss of light received from the LEDs 414 and 416 went a liquid in the ramp 335 passes over the apertures 364 and 368, respectively, and signal the timing circuit 426 via signal lines 432 and 434, respectively. If the flowable food or liquid is clear, an additive to darken or opaque the flowable food or liquid can be added. An example of such an additive is opaque black food coloring, such as Kopykake Kroma Kolors sold by Kopykake Enterprises in Street Torrance, Calif., or barium sulfate suspension, such as sold by Spectrum Chemical in New Brunswick, N.J.

A data transmit circuit 428 is included on the PCB 400 for transmitting timing results by the timing circuit 426 to an external computer via data line 408 and out data port 340, such as a USB port. A reset button 444 is located within cutout 328 of the cover plate 304 to reset the timer circuit 426 and display 402 after each timing interval. The reset button 444 is connector to the PCB 400 via wire 446 to a reset circuit 430 which resets the timer circuit 426 and display 402 to zero when the reset button 444 is pressed. The LEDs 414 and 416 and PCB 400 and connected components are preferably powered by internal batteries 412.

Figure 14:
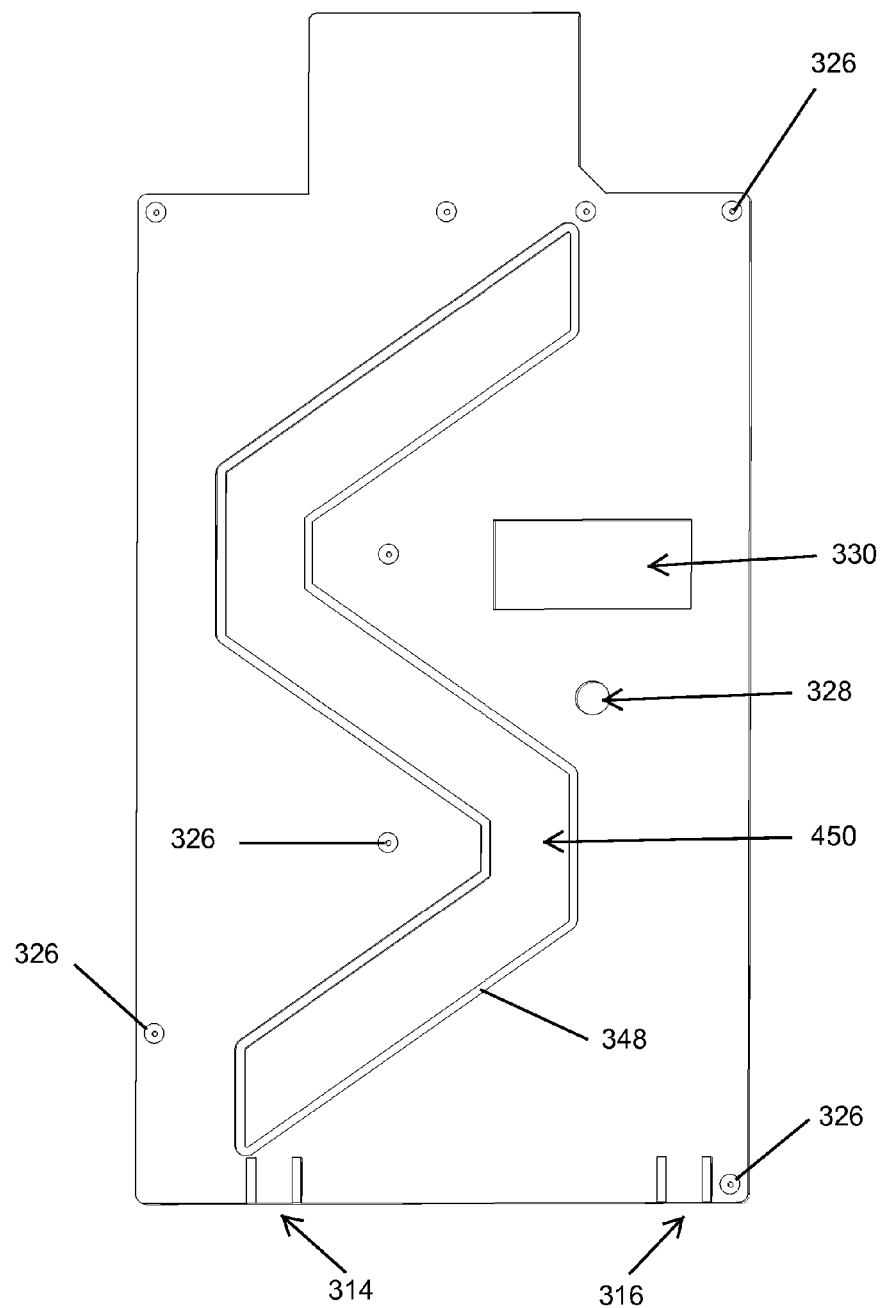
FIG. 14 is front view of the cover plate of the flow rate measuring device shown in FIGS. 5-7.

FIG. 14 is a front view of the cover plate 304 shown in FIGS. 5-7. The cover plate 304 includes cutout 330 for a timer display and cutout 328 for a reset button. Screw holes 326 including concave openings for screw heads are located at multiple locations on the cover plate 304 to secure the cover plate 304 to the body 302 of the flow rate measuring device 300.

Slots 314 and 316 for the legs 310 and 312 are shown on the bottom of the cover plate 304. A zigzag cutout 450 also is included on the cover plate 304 to allow the ramp 335 to be inserted into the receptacle 345 of the measuring device 300. A ridge 348 is included in the periphery of the cutout 450 to provide a tight seal and prevent ambient light from entering the receptacle 345.

Figure 15:
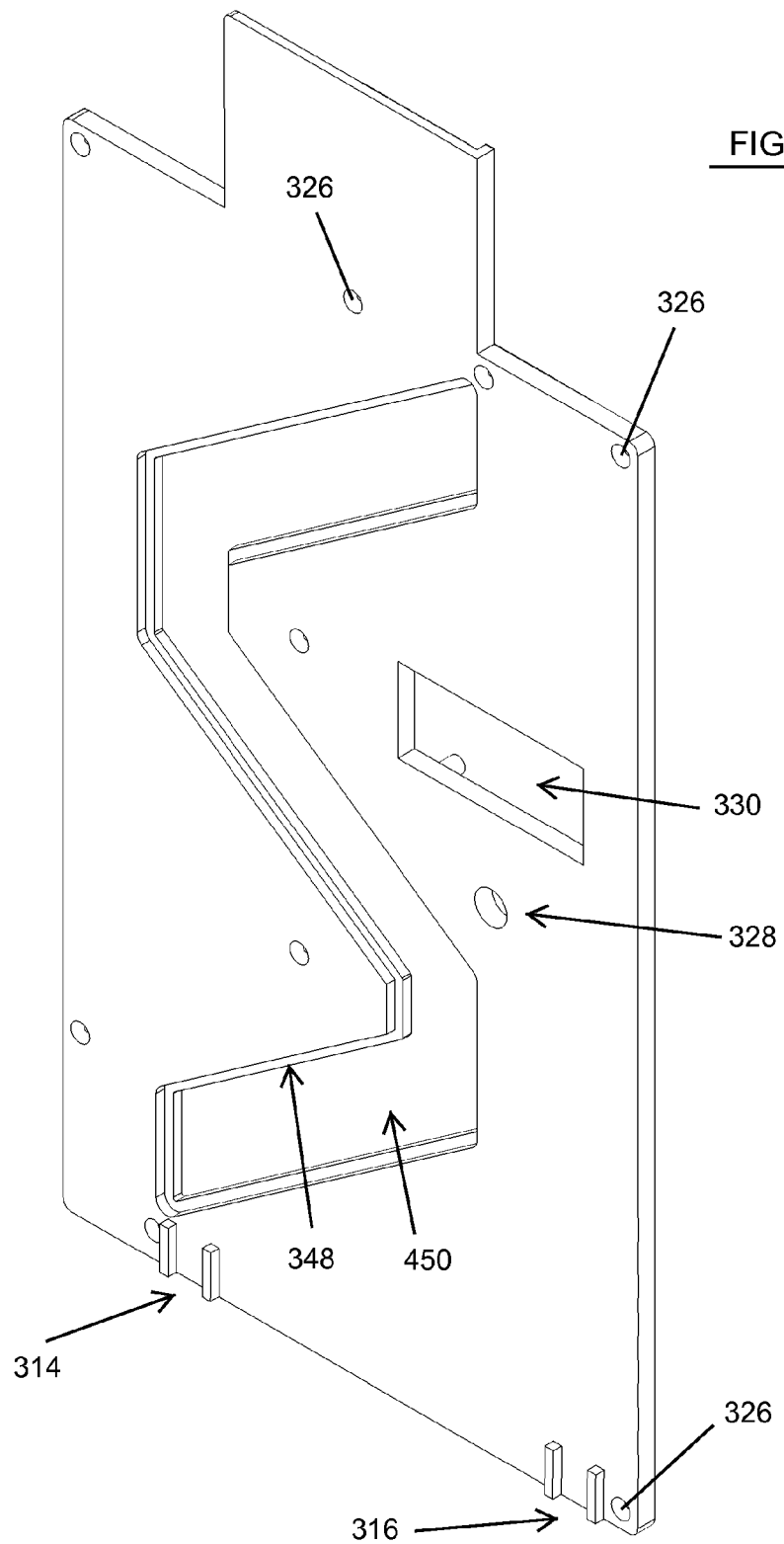
FIG. 15 is a perspective view of the cover plate shown in FIG. 14.

FIG. 15 is a perspective view of the cover plate 304 shown in FIG. 14.

Figure 16:
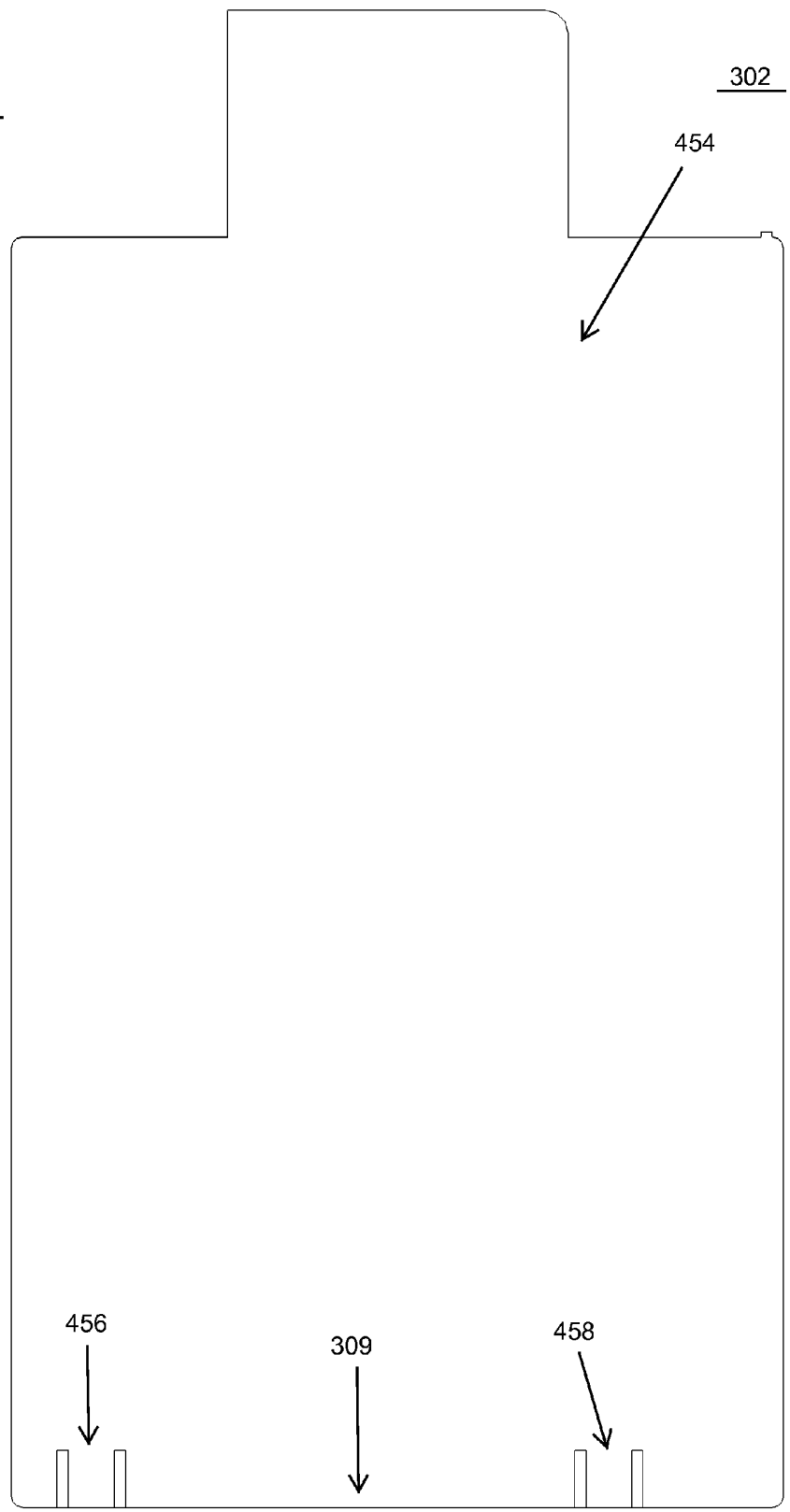
FIG. 16 is a back view of the flow rate measuring device show in FIGS. 8-12.

FIG. 16 is a back view of the flow rate measuring device 300 shown in FIGS. 5-7. The back 454 is of the body 302 shown having slots 456 and 458 for the stabilizer legs 310 and 312 at the bottom 309 of the measuring device 300.

Figure 17:
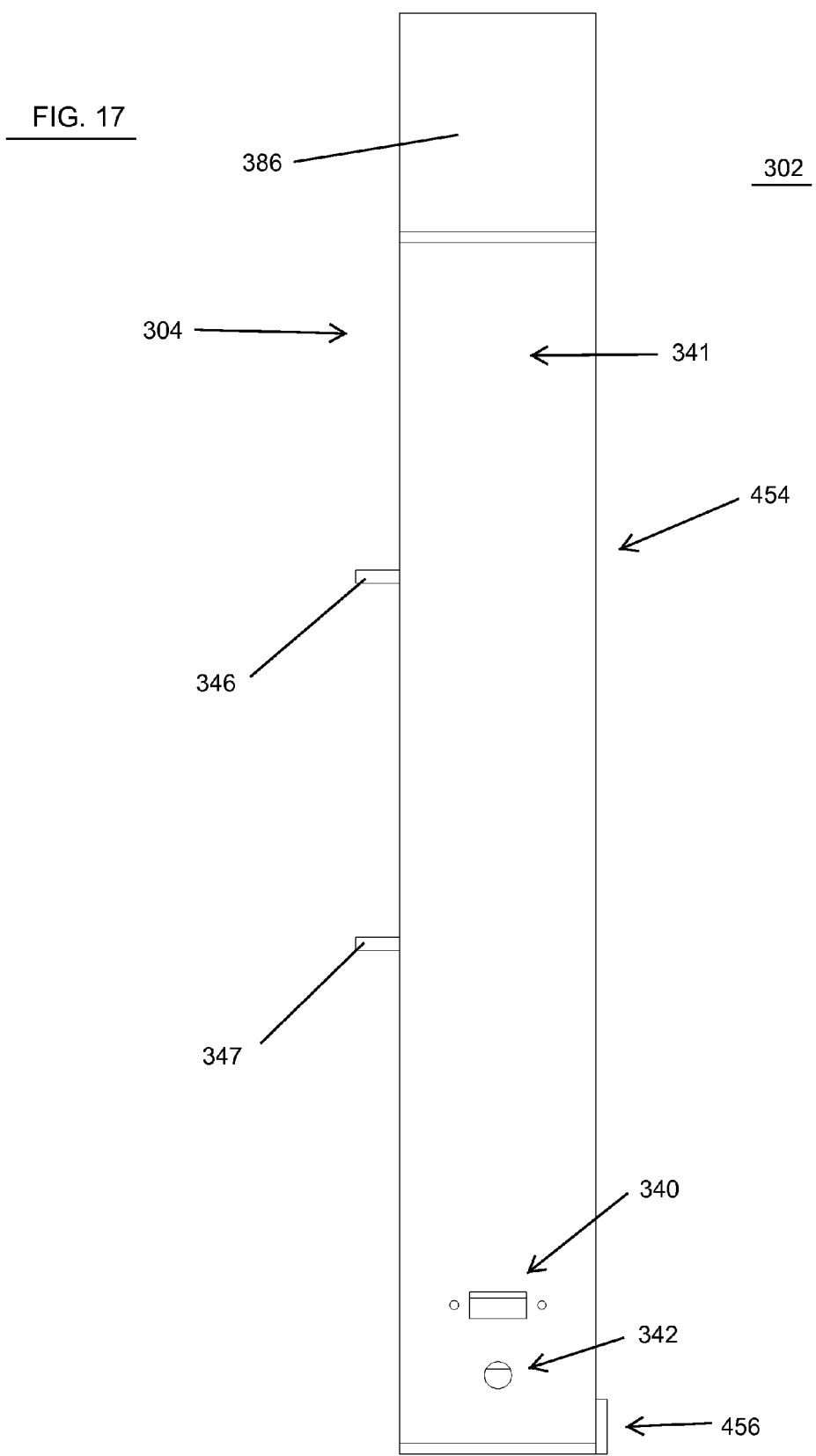
FIG. 17 is a side view of the flow rate measuring device shown in FIGS. 8-12.

FIG. 17 is a side view of a first side 341 of the body 302 of the measuring device 300. The first side 341 includes the cutout 340 for a data input/output and cutout 342 for an on/off switch or external power source input. Mounting posts 346 and 347 are shown extending beyond the body 302. The slot 456 on the back 454 of body 302 also can be seen. The back splash 386 is shown at the upper portion 319.

Figure 18:
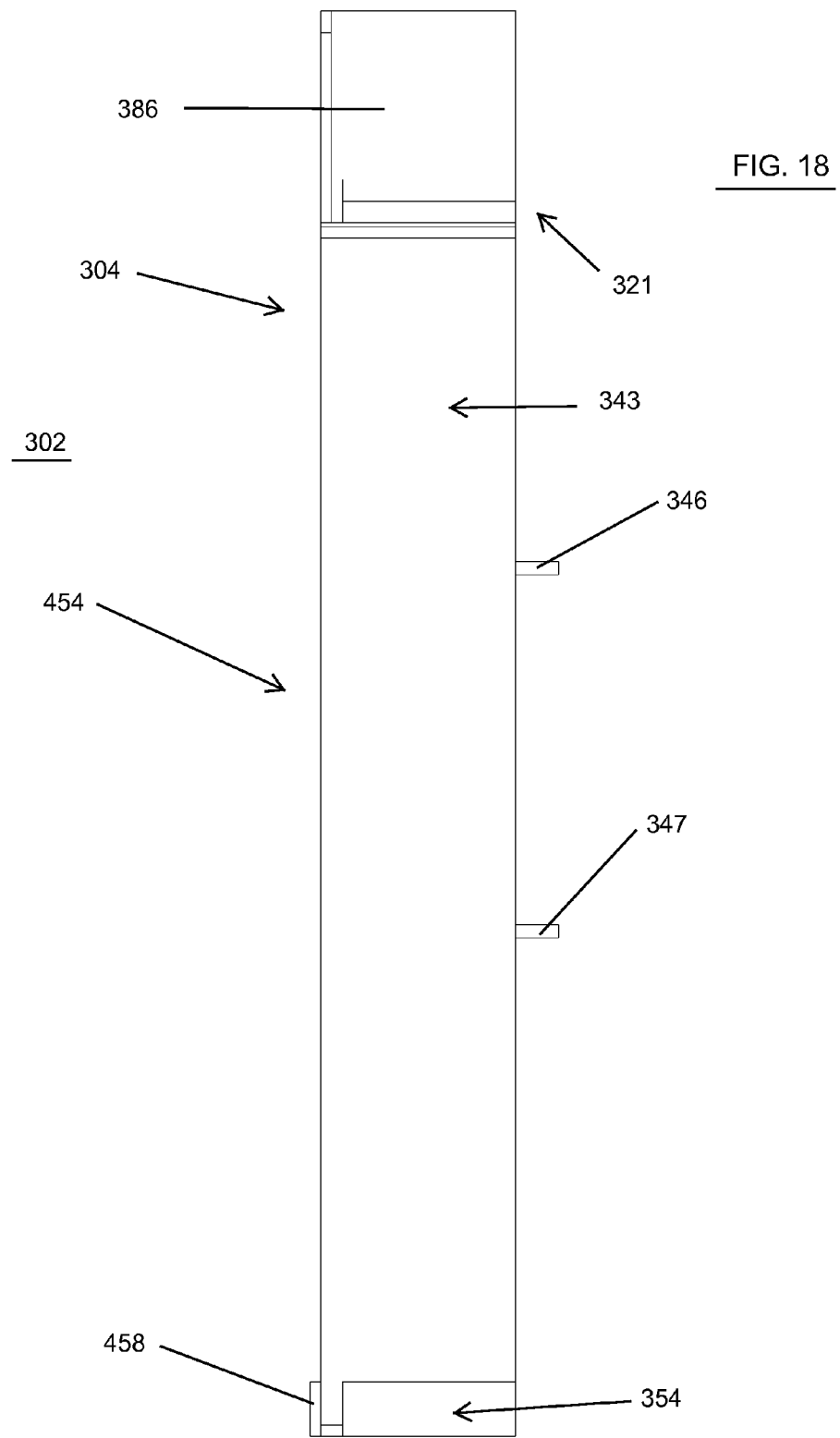
FIG. 18 is an opposing side view of the flow rate measuring device shown in FIGS. 8-12.

FIG. 18 is a side view of an opposing second side 343 of the body 302 of the flow rate measuring device 300 shown in FIGS. 5-7. Illustrated are the mounting posts 346 and 347 and back splash 386. Also shown is the opening 354 at the bottom 309 of the body 302. The pivot mount 321 and slot 458 also are shown.

Figure 19:
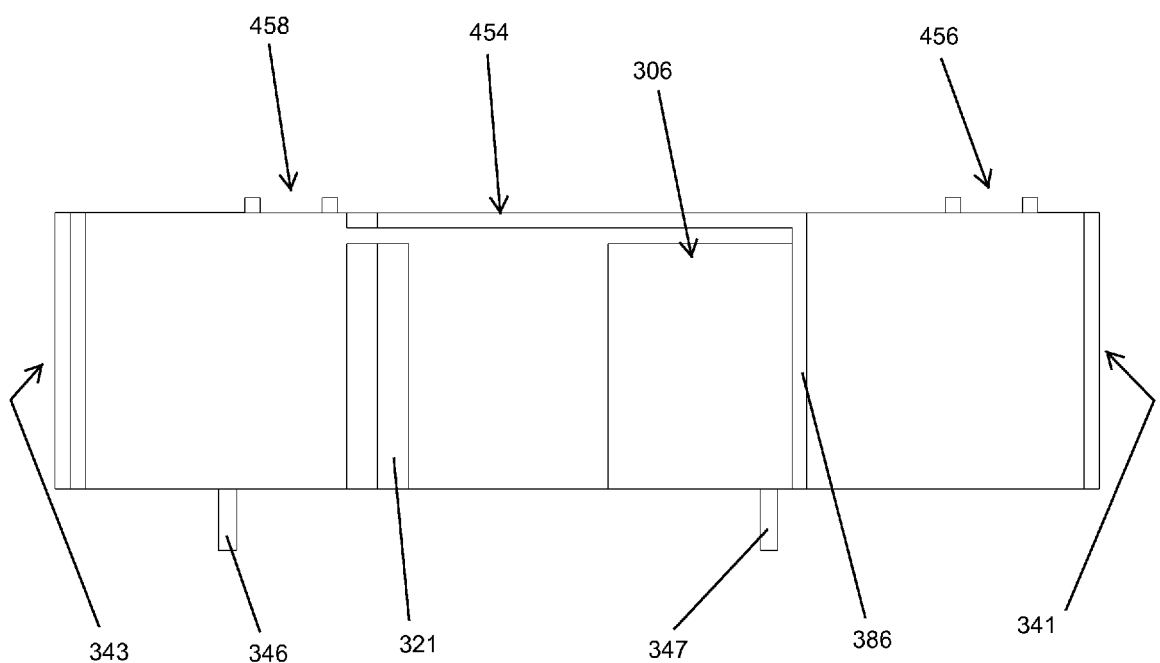
FIG. 19 is a top view of the flow rate measuring device shown in FIGS. 8-12.

FIG. 19 is a top view of the body 302 of the measuring apparatus 300 shown in FIGS. 8-11. Illustrated is the pivot mount 321 for the tip cup 318, the input port 306, and splash wall 386. Also illustrated are the slots 456 and 458 for the stabilizing legs 310 and 312. Mounting posts 346 and 347 are shown. Back 454 and sides 341 and 343 of the body 302 of the measuring device 300 are further shown.

Figure 20:
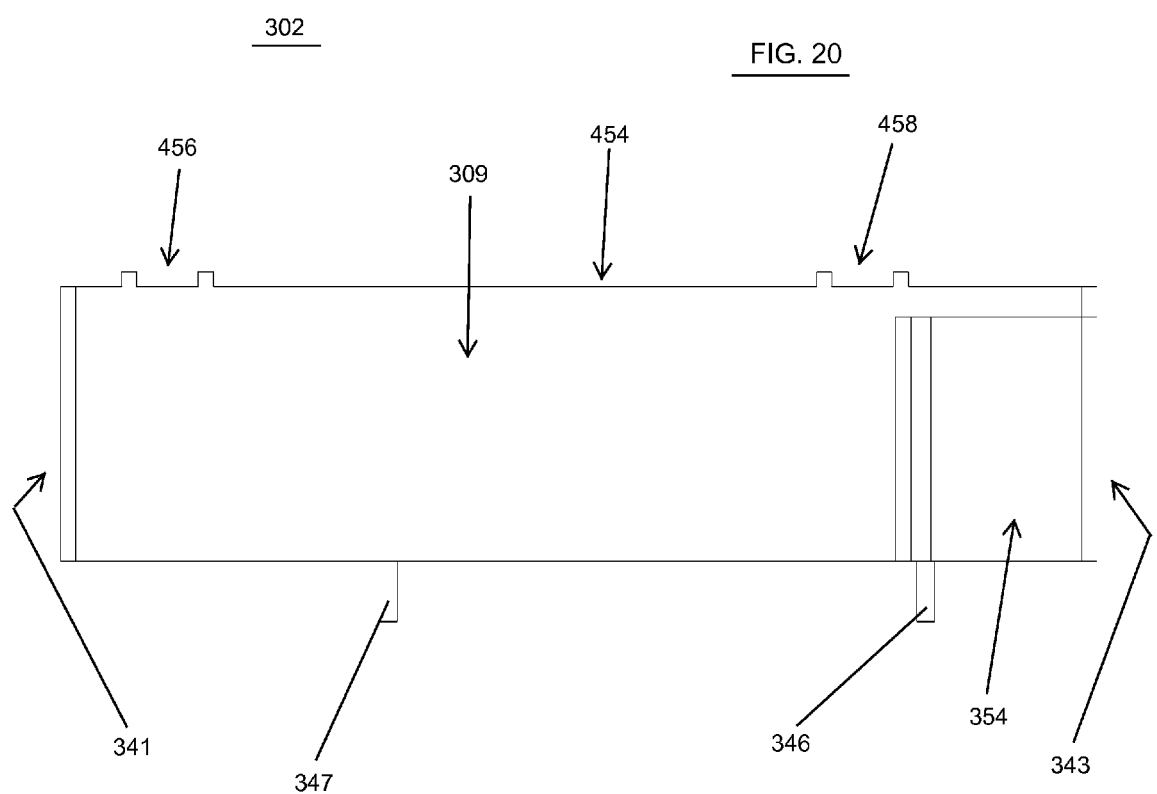
FIG. 20 is a bottom view of the flow rate measuring device shown in FIGS. 8-12.

FIG. 20 is a bottom view of the body 302 of the measuring apparatus 300 shown in FIGS. 8-11. Illustrated are the mounting posts 346 and 347 and slots 456 and 458 for the stabilizing legs 310 and 312. Back 454 and sides 341 and 343 of the body 302 of the measuring device 300 are further shown. Finally, the opening 354 for the catch tray 308 is shown.

Figure 21:
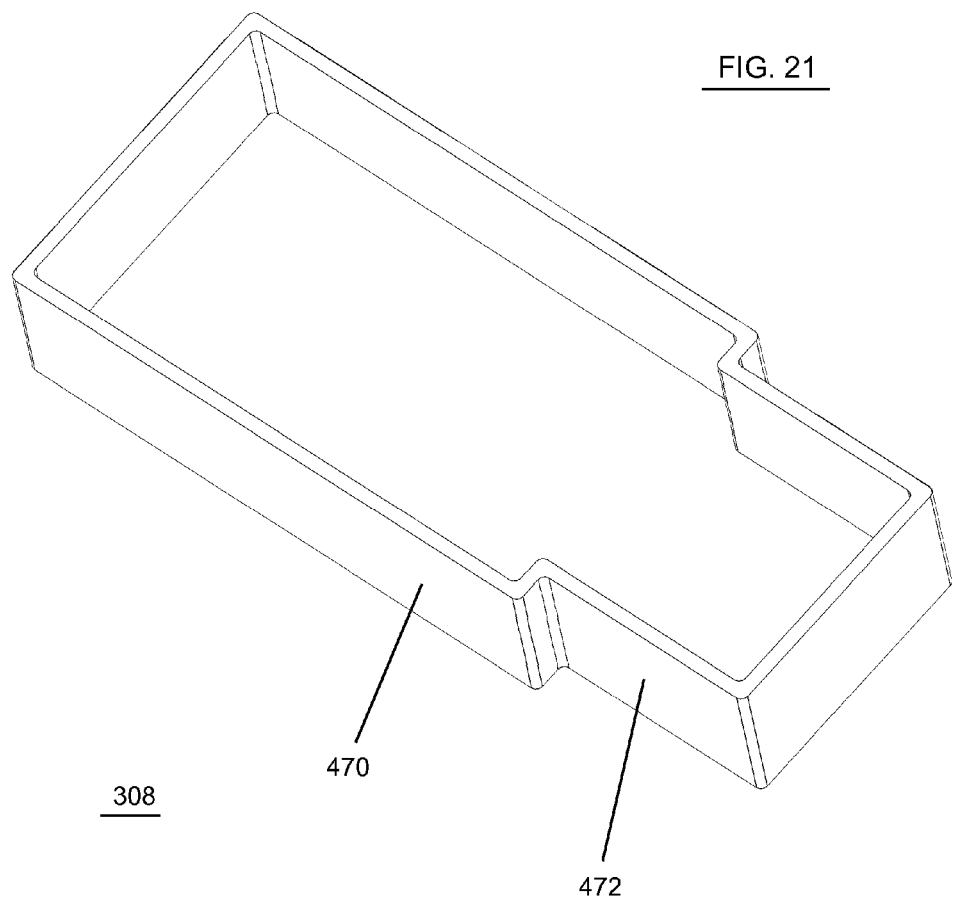
FIG. 21 is a perspective view of the catch tray of the flow rate measuring device shown in FIGS. 5-7.

FIG. 21 illustrates the catch tray 308 shown in FIG. 5. The catch tray 308 includes a wider width section 470 and a smaller width section 472. The smaller width section 472 is sized to fit into the opening 354.

Figure 22:
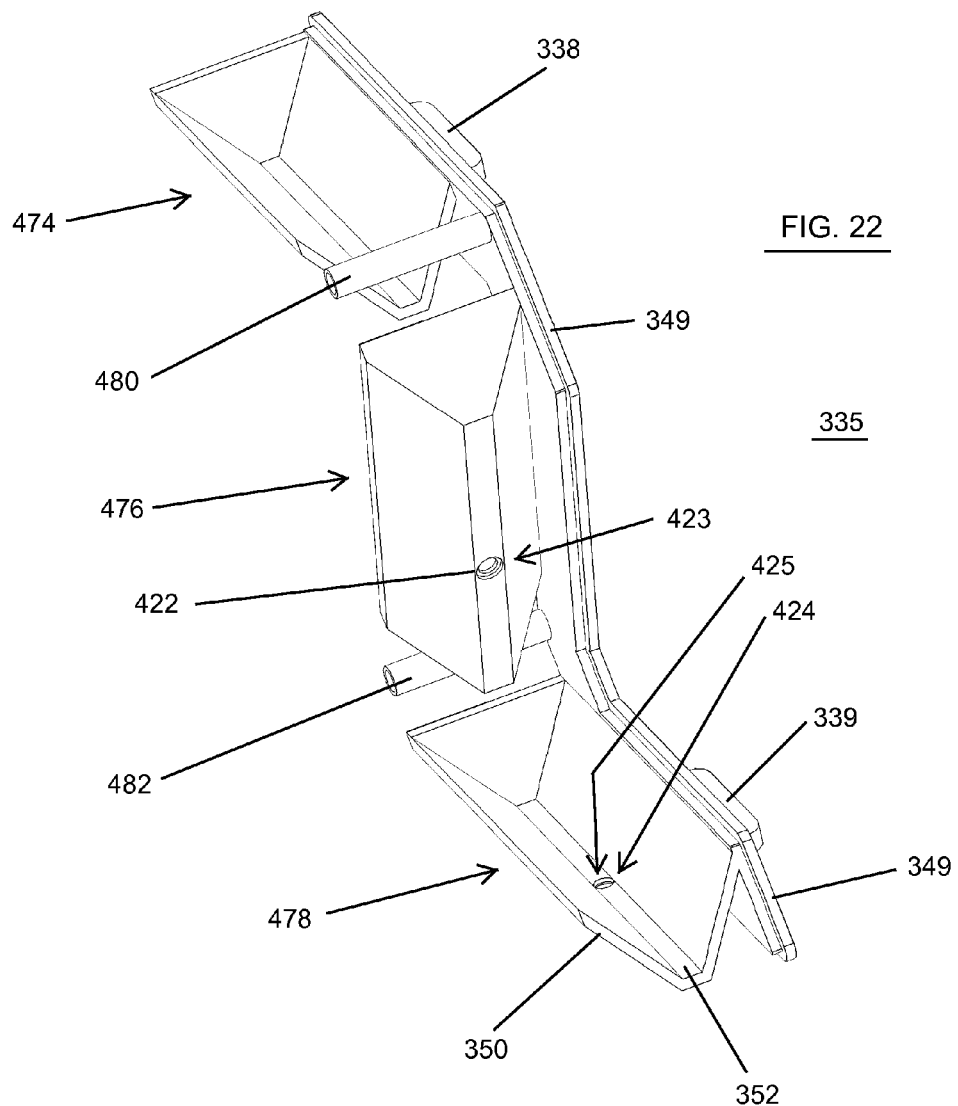
FIG. 22 is a perspective view of the ramp shown in FIG. 7 of the flow rate measuring device.
Figure 23:
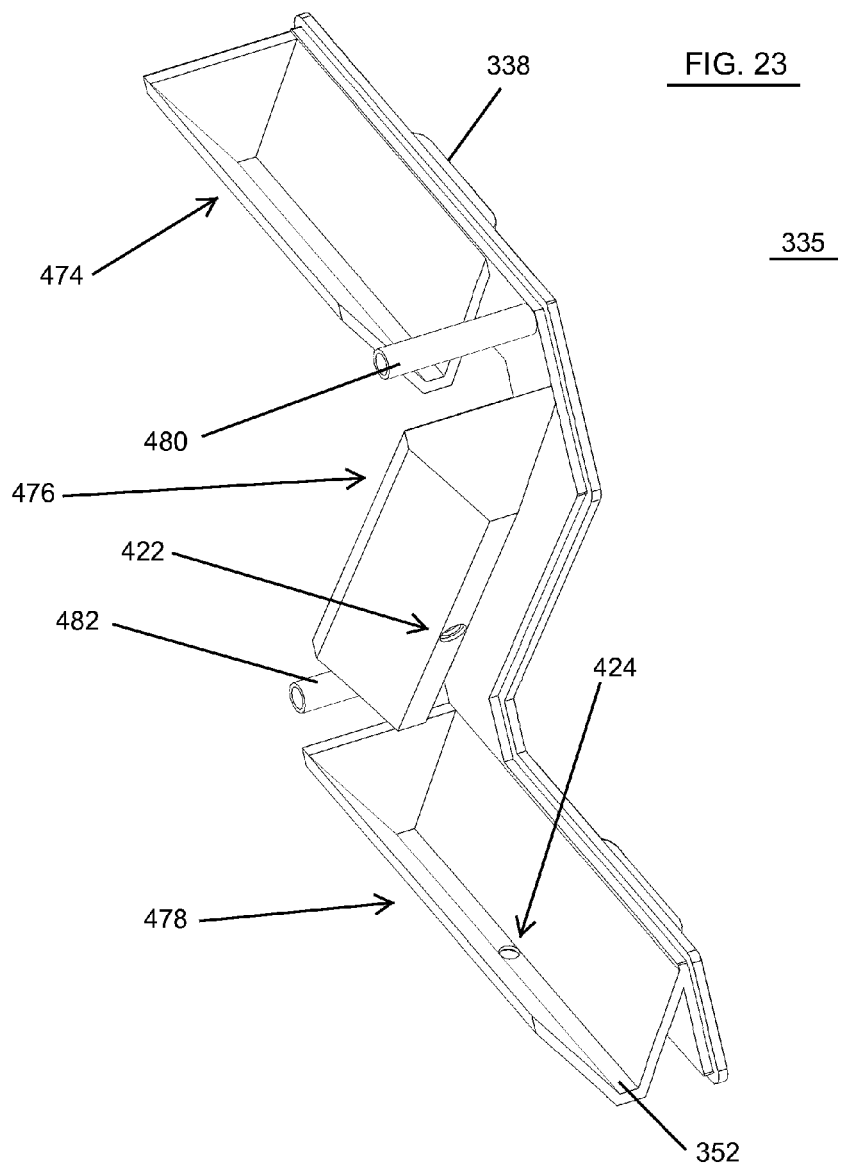
FIG. 23 is a perspective view from a different angle of the ramp shown in FIG. 22 of the flow rate measuring device.
Figure 24:
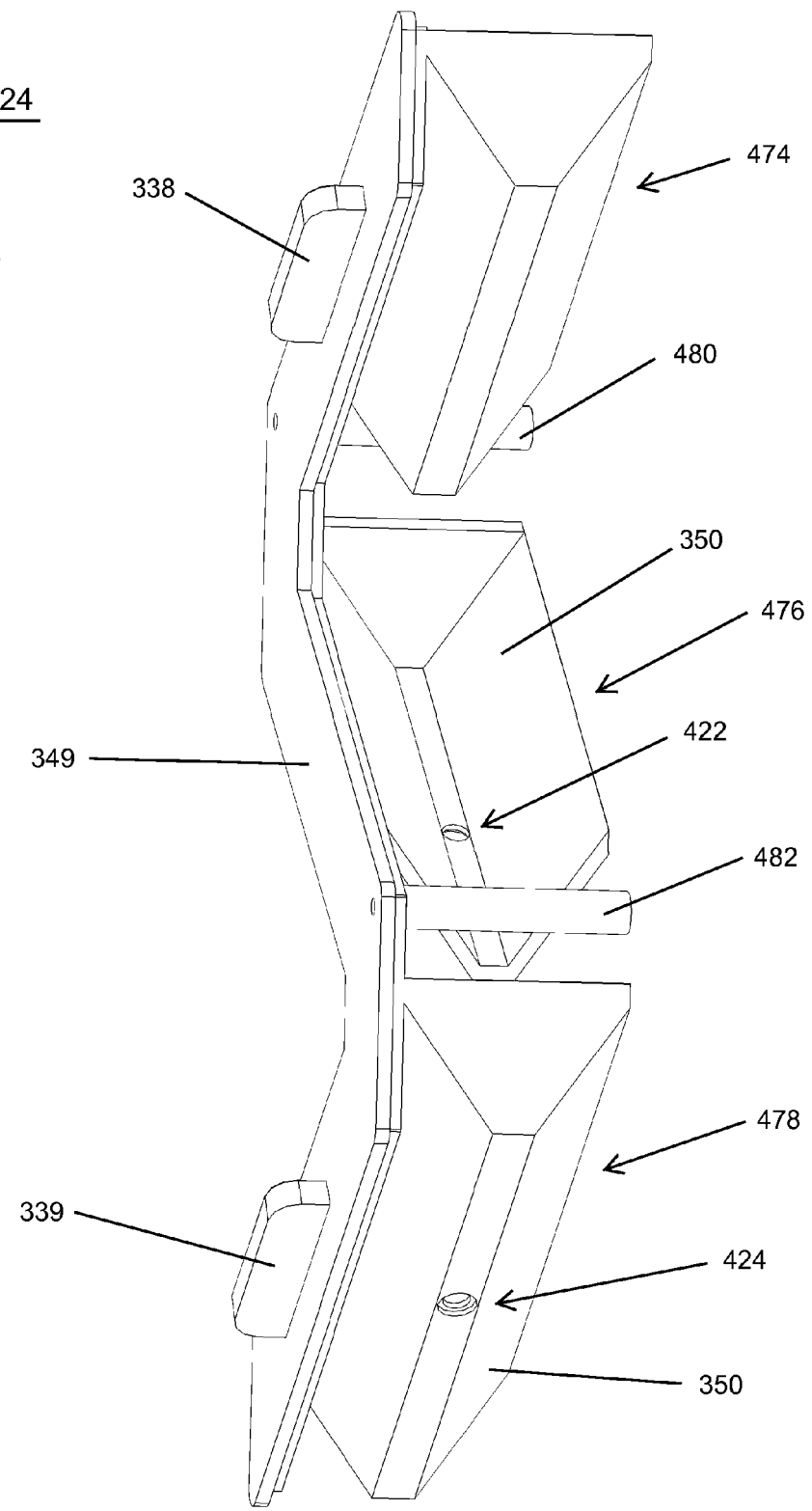
FIG. 24 is a perspective view from a different angle of the ramp shown in FIGS. 22 and 23 of the flow rate measuring device.

FIGS. 22-24 are perspective views from different angles of the removable ramp 335 shown in FIG. 7. FIG. 22 is a front perspective view of the ramp 335, FIG. 23 is a front perspective view of the ramp 335 from a slightly different angle, and FIG. 24 is a rear perspective view of the ramp 335. The ramp 335 in a preferred embodiment includes three individual chutes 474, 476, and 478. The second and third chutes 476 and 478 include apertures 422 and 424, respectively. The apertures 422 and 424 include a transparent plate or cover 423 and 425, respectively, which are level and flush with the surface of the floor 352 in the chutes 476 and 478. Of course, the chutes 476 and 478 can be constructed of completely transparent material, or have portions of transparent material over the photo detectors 404 and 406. In the preferred embodiment, the transparent plates 423 and 425 allow the photo detectors 404 and 406 to detect when a liquid passes over the apertures 422 and 424 by blocking or at least decreasing the light passing through the apertures 422 and 424 from the artificial light sources 414 and 416.

The first, second and third chutes 474, 476, and 478, respectively, are mounted to the cover plate 349 of the ramp 335. Mounting tubes 480 and 482 are connected to the cover plate 349 and function to properly locate and secure the ramp 335 inside the receptacle 345 of the housing 301 of the flow rate measuring device 300 by fitting over mounting posts 346 and 347, respectively. The chutes 474, 476, and 478 are mounted in a zigzag configuration to lengthen the ramp 335 in a smaller area and control flowable food or liquid flowing down chutes 474,476,478. A liquid or flowable food to be tested first enters chute 474 after entering the input port 306 of the measuring device 300. The fluid then flows down chute 474, then to chute 476, and finally chute 478. As the liquid passed over the aperture 422 and then aperture 424, photo detectors 404,406 detect the liquid passing over the apertures 422,424, and send detection signals to the timing circuit 426, which displays the elapsed time for the liquid to pass between the apertures 422 and 424 on the display 402.

After chute 478, the liquid or flowable food flows into the catch tray 308. The ramp 335 with chutes 473,476,478 can be easily removed for cleaning after each test by unscrewing the securing knobs 336 and 337. The tip cup 318 and catch tray 308 also can easily be removed for cleaning. The ramp 335, catch tray 308, and tip cup 318 are preferably constructed of plastic which can be easily cleaned by rinsing with water. The housing 301 also preferably can be constructed of molded plastic for reduced cost and weight. The chutes 474,476,478 preferably have a V cross section with a flat floor 352 bottom so that flowing liquid of flowable food covers the apertures 422 and 424 as the liquid or flowable food flows down the ramp 335.

It should be understood that the above description of the present invention and preferred embodiment are given by way of description and illustration, and not limitation. Many changes and modifications within the scope of the present invention may be made without departing from the spirit of the present invention, and the present invention includes all such changes and modifications.

The invention claimed is:
1. A flow rate measuring device, comprising:
  a ramp having an upper portion and a lower portion enabling a flowable substance to flow between the upper portion and the lower portion;
  a first photo detector located proximate the upper portion of the ramp for detecting when a flowable substance passes by the first photo detector;

a second photo detector located proximate the lower portion of the ramp for detecting when a flowable substance passes by the second photo detector; and a timing circuit connected to the first photo detector and the second photo detector, wherein the timing circuit determines amount of time for a flowable substance to flow between the first photo detector and the second photo detector.

2. The flow rate measuring device of claim 1, wherein the flowable substance is a flowable food.

3. The flow rate measuring device of claim 1, further comprising:
a substance to be added to a flowable substance in order to opaque a flowable substance that is transparent.

4. The flow rate measuring device of claim 1, wherein the ramp includes opposing angled side walls and a floor between a bottom of the opposing angled side walls.

5. The flow rate measuring device of claim 1, wherein a cross-section of the ramp and opposing side walls has a V-shaped configuration.

6. The flow rate measuring device of claim 1, wherein the ramp comprises multiple sub-ramps in a zigzag configuration.

7. The flow rate measuring device of claim 1, wherein the ramp comprises multiple disconnected sub-ramps in a cascading configuration.

8. The flow rate measuring device of claim 1, further comprising:
a first light source directed toward the first photo detector; and
a second light source directed toward the second photo detector.

9. The flow rate measuring device of claim 8, wherein the ramp is enclosed within a housing to prevent ambient light from reaching inside the ramp, and the ramp is removable from the housing for cleaning.

10. The flow rate measuring device of claim 8, further comprising:
a third mounting bracket for securing the first light source above first photo detector; and
a fourth mounting bracket for securing the second light source above the second photo detector.

11. The flow rate measuring device of claim 1, further comprising:
communication circuitry enabling the timing circuit to transmit timing data to a computer; and
a data port enabling a computer to electronically connect to the communication circuitry and receive timing data from the timing circuit.

12. The flow rate measuring device of claim 1, further comprising:
a pivotally mounted tip cup for pouring a flowable substance into a top of the ramp.

13. The flow rate measuring device of claim 1, further comprising:
a syringe for injecting a flowable substance onto a top of the ramp.

14. The flow rate measuring device of claim 1, wherein the first photo detector and the second photo detector are located below the ramp, and portions of the ramp over the first photo detector and the second photo detector are transparent so as to enable the first photo detector and the second photo detector to detect when a flowable substance in the ramp passes over the first photo detector and the second photo detector.

15. The flow rate measuring device of claim 14, further comprising:
a first mounting bracket for securing the first photo detector below the upper portion of the ramp; and
a second mounting bracket for securing the second photo detector below the lower portion of the ramp.

16. A flow rate measuring device, comprising:
a housing for enclosing and preventing a ramp from being exposed to ambient light;
a ramp removable from the housing having an upper transparent portion and a lower transparent portion enabling a flowable substance to flow therebetween;
a first photo detector below the upper transparent portion for detecting a flowable substance passing over the first photo detector and a second photo detector below the lower transparent portion for detecting a flowable substance passing over the second photo detector; and
a timing circuit connected to the first photo detector and the second photo detector, wherein the timing circuit determines amount of time for a flowable substance to flow between the first photo detector and the second photo detector.

17. The flow rate measuring device of claim 16, further comprising:
a first light source over the first photo detector; and
a second light source over the second photo detector.

18. The flow rate measuring device of claim 16, further comprising:
a display on the housing for displaying elapsed time for a flowable substance to flow between the first photo detector and the second photo detector as determined by the timing circuit.

19. A flow rate measuring device, comprising:
a ramp having an upper portion and a lower portion enabling a flowable substance to flow between the upper portion and the lower portion;
a first liquid detector located proximate the upper portion of the ramp for detecting when a flowable substance passes by the first liquid detector;
a second liquid detector located proximate the lower portion of the ramp for detecting when a flowable substance passes by the second liquid detector; and
a timing circuit connected to the first liquid detector and the second liquid detector, wherein the timing circuit determines amount of time for a flowable substance to flow between the first liquid detector and the second liquid detector.

20. The flow rate measuring device of claim 19, wherein the first liquid detector includes a photo detector, and the second liquid detector includes a photo detector.

* * * * *